United States Patent
Craig et al.

(10) Patent No.: US 10,968,480 B2
(45) Date of Patent: *Apr. 6, 2021

(54) ALPHA-HEMOLYSIN VARIANTS AND USES THEREOF

(71) Applicant: Roche Sequencing Solutions, Inc., Pleasanton, CA (US)

(72) Inventors: Timothy K. Craig, Campbell, CA (US); Mark R. Ambroso, San Jose, CA (US); Corissa J. Harris, Santa Clara, CA (US); Matthew M. Dipietro, Gilroy, CA (US); Yaozhong Zou, Sunnyvale, CA (US); Marshall W. Porter, Santa Clara, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/425,743

(22) Filed: May 29, 2019

(65) Prior Publication Data

US 2019/0367975 A1 Dec. 5, 2019

Related U.S. Application Data

(63) Continuation of application No. 15/492,214, filed on Apr. 20, 2017, now Pat. No. 10,351,908.

(60) Provisional application No. 62/325,749, filed on Apr. 21, 2016.

(51) Int. Cl.
| | |
|---|---|
| C07K 14/31 | (2006.01) |
| C12Q 1/6869 | (2018.01) |
| C12Q 1/689 | (2018.01) |
| G01N 33/487 | (2006.01) |
| G01N 27/447 | (2006.01) |

(52) U.S. Cl.
CPC ............ *C12Q 1/6869* (2013.01); *C07K 14/31* (2013.01); *C12Q 1/689* (2013.01); *G01N 27/44791* (2013.01); *G01N 33/48721* (2013.01); *C12Q 2600/156* (2013.01); *G01N 2333/31* (2013.01)

(58) Field of Classification Search
CPC ..................................................... C07K 14/31
See application file for complete search history.

(56) References Cited

U.S. PATENT DOCUMENTS

| | | | |
|---|---|---|---|
| 10,227,645 B2* | 3/2019 | Craig | C07K 14/31 |
| 10,351,908 B2* | 7/2019 | Craig | C12Q 1/689 |
| 2017/0088588 A1 | 3/2017 | Dorwart | |
| 2017/0088890 A1 | 3/2017 | Craig | |

FOREIGN PATENT DOCUMENTS

| | | |
|---|---|---|
| WO | 2006028508 A2 | 3/2006 |
| WO | 2010004265 A1 | 1/2010 |
| WO | 2010055307 A1 | 5/2010 |
| WO | 2010109197 A2 | 9/2010 |
| WO | 2012083249 A2 | 6/2012 |
| WO | 2013123450 A1 | 8/2013 |
| WO | 2014074727 A1 | 5/2014 |
| WO | 2015061510 A1 | 4/2015 |
| WO | 2017167811 A1 | 10/2017 |

OTHER PUBLICATIONS

Akeson, et al., "Microsecond Time-Scale Discrimination Among Polycytidylic Acid, Polyadenylic Acid, and Polyuridylic Acid as Homopolymers or as Segments Within RNA Molecules", Biophysical Journal, Dec. 1999, pp. 3227-3233, vol. 77.

Aksimentiev, et al., "Imaging a-Hemolysin with Molecular Dynamics: Ionic Conductance, Osmotic Permeability, and the Electrostatic Potential Map", Biophys J. Jun. 2005;88(6):3745-61. Epub Mar. 11, 2005.

Ausubel, et al., "Current Protocols in Molecular Biology", John Wiley & Sons Inc., 1987-1994,1.

Butler, et al., "Single-molecule DNA detection with an engineered MspA protein nanopore", Proc Natl Acad Sci USA. Dec. 30, 2008;105(52):20647-52. Epub Dec. 19, 2008.

Fyta, M., "Threading DNA through nanopores for biosensing applications", Journal of Physics: Condensed Matter, Institute of Physics Publishing, Bristol, GB, vol. 27, No. 27, doi:10.1088/0953-8984/27/27/273101, ISSN 0953-8984, (Jun. 10, 2015), p. 273101, (Jun. 10, 2015), XP020287187.

Giovanni, et al., "Enhanced translocation of single DNA molecules through alpha-hemolysin nanopores by manipulation of internal charge", Proceedings National Academy of Sciences PNAS, National Academy of Sciences, US, vol. 105, No. 50, doi:10.1073/PNAS.0808296105, ISSN 0027-8424, (Dec. 16, 2008), pp. 19720-19725, (Dec. 5, 2008), XP002568390.

(Continued)

*Primary Examiner* — Karen Cochrane Carlson
(74) *Attorney, Agent, or Firm* — FisherBroyles, LLP; Victoria L. Boyd; Jason M. Pass

(57) ABSTRACT

Described herein are variants of alpha-hemolysin having at least one mutation, such as a mutation to a positive charge. In certain examples, the mutation is selected from V149K, E287R, H35G, T109K, P151K, K147N, E111N, M113A, or combinations thereof in the mature, wild-type alpha-hemolysin amino acid sequence. The α-hemolysin variants may also include a substitution at H144A and/or a series of glycine residues spanning residues 127 to 131 of the mature, wild-type alpha hemolysin. Also provided are nanopore assemblies including the alpha-hemolysin variants, the assembly having a decreased time-to-thread. The decreased time-to-thread, for example, increases DNA sequencing efficiency and accuracy.

23 Claims, 2 Drawing Sheets

Specification includes a Sequence Listing.

(56) References Cited

OTHER PUBLICATIONS

Gu, et al., "Prolonged residence time of a noncovlent molecular adapter, beta-cyclodextrin, within the lumen of mutant alpha-hemolysin pores", J. Gen. Physiol. 2007 118: 481-493.

Howorka, et al., "Kinetics of duplex formation for individual DNA strands within a single protein nanopore", Proc Natl Acad Sci U S A. Nov. 6, 2001;98(23):12996-3001. Epub Oct. 23, 2001.

Howorka, et al., "Sequence-specific detection of individual DNA strands using engineered nanopores", Nature Biotechnology Jul. 2001;19(7):636-9.

International Preliminary Report on Patentability issued in PCT/US2017/028636 dated Oct. 23, 2018 (15 pages).

International Search Report and Written Opinion dated Oct. 26, 2017 for PCT/US2017/028636.

International Search Report and Written Opinion dated Sep. 14, 2017 in corresponding PCT/ EP2015/053681,pp. 1-23.

Kasianowicz, et al., "Characterization of individual polynucleotide molecules using a membrane channel", Proc Natl Acad Sci U S A. Nov. 26, 1996;93(24):13770-3.

Li, et al., "Structural Analysis and Optimization of the Covalent Association between SpyCatcher and a Peptide Tag", Journal of Molecular Biology, 2014, 426:309-317.

Meller, et al.,"Voltage-Driven DNA Translocations through a Nanopore", Phys Rev Lett. Apr. 9, 2001;86(15):3435-8.

Movileanu, et al., "Detecting protein analytes that modulate transmembrane movement of a polymer chain within a single protein pore", Nat Biotechnol. Oct. 2000;18(10):1091-5.

Nakane, et al., "A Nanosensor for Transmembrane Capture and Identification of Single Nucleic Acid Molecules", Biophys J. Jul. 2004;87(1):615-21.

Rhee, et al., "Nanopore sequencing technology: nanopore preparations", Trends Biotechnol. Apr. 2007;25(4):174-81. Epub Feb. 22, 2007.

Sambrook, et al., "Molecular Cloning a Laboratory Manual, Molecular Cloning: A Laboratory Manual", 1989, Cover, Bibliography, Table of Contents, Third Edition, Cold Spring Harbor Laboratory Press.

Singleton, et al., Dictionary of Microbiology and Molecular Biology, 2D Ed., John Wiley and Sons, Mew York (1994).

Song, et al., "Structure of Staphylococcal a-Hemolysin, a Heptameric Transmembrane Pore", Science. Dec. 13, 1996;274(5294):1859-66.

Stoddart, et al., "Single-nucleotide discrimination in immobilized DNA oligonucleotides with a biological nanopore", Proc Natl Acad Sci USA. May 12, 2009;106(19):7702-7. doi: 10.1073/pnas.0901054106. Epub Apr. 20, 2009.

Sun, et al., "Langevin dynamics simulation on the translocation of polymer through-hemolysin pore", Journal of Physics: Condensed Matter, Institute of Physics Publishing, Bristol, GB, vol. 26, No. 41, doi:10.1088/0953-8984/26/41/415101, ISSN 0953-8984, (Sep. 5, 2014), p. 415101, (Sep. 5, 2014), XP020271234.

Office Action dated Aug. 28, 2020 for European Applicaiton No. 17 724 146.0.

* cited by examiner

ALPHA-HEMOLYSIN VARIANTS AND USES THEREOF

CROSS-REFERENCE TO RELATED APPLICATIONS

This application is a continuation of U.S. patent application Ser. No. 15/492,214, filed Apr. 20, 2017, which claims the benefit of priority to U.S. Provisional Application No. 62/325,749, filed Apr. 21, 2016, each of which is incorporated herein in their entirety.

SEQUENCE LISTING

The instant application contains a Sequence Listing which has been submitted electronically in ASCII format and is hereby incorporated by reference in its entirety. Said ASCII copy, created on Feb. 20, 2019, is named 04338-538US2_SeqListing.txt and is 42 kilobytes in size.

TECHNICAL FIELD

Disclosed are compositions and methods relating to Staphylococcal aureaus alpha-hemolysin variants. The alpha-hemolysin (α-HL) variants are useful, for example, as a nanopore component in a device for determining polymer sequence information. The nanopores, methods, and systems described herein provide quantitative detection of single strand nucleic acids, such as DNA, RNA, etc., employing nanopore-based single-molecule technology with improved characteristics.

BACKGROUND

Hemolysins are members of a family of protein toxins that are produced by a wide variety of organisms. Some hemolysins, for example alpha hemolysins, can disrupt the integrity of a cell membrane (e.g., a host cell membrane) by forming a pore or channel in the membrane. Pores or channels that are formed in a membrane by pore forming proteins can be used to transport certain polymers (e.g., polypeptides or polynucleotides) from one side of a membrane to the other.

Alpha-hemolysin (α-HL, a-HL or alpha-HL) is a self-assembling toxin which forms a channel in the membrane of a host cell. Alpha-HL has become a principal component for the nanopore sequencing community. It has many advantageous properties including high stability, self-assembly, and a pore diameter which is wide enough to accommodate single stranded DNA but not double stranded DNA (Kasianowicz et al., 1996).

Previous work on DNA detection in the a-HL pore has focused on analyzing the ionic current signature as DNA translocates through the pore (Kasianowicz et al., 1996, Akeson et al., 1999, Meller et al., 2001), a very difficult task given the translocation rate (~1 nt/µs at 100 mV) and the inherent noise in the ionic current signal. Higher specificity has been achieved in nanopore-based sensors by incorporation of probe molecules permanently tethered to the interior of the pore (Howorka et al., 2001a and Howorka et al., 2001b; Movileanu et al., 2000).

The wild-type a-HL results in significant number of deletion errors, i.e. bases are not measured. Therefore, α-HL nanopores with improved properties are desired.

BRIEF SUMMARY OF THE INVENTION

As described herein, provided are mutant staphylcoccal alpha hemolysin (αHL) polypeptide containing an amino acid variation that enhances the time to thread, e.g., decreases the time to capture of the molecule of interest. For example, the disclosed variants reduce the time to thread of the molecule of interest, e.g., various tagged nucleotides or a nucleotide to be sequenced.

In certain example aspects, the α-hemolysin (α-HL) variants comprise a substitution at a position corresponding to any one of V149K, E287R, H35G, T109K, P151K, K147N, E111N, M113A, or combinations thereof of SEQ ID NO: 14 (the mature, wild-type alpha hemolysin sequence). The substitution of the α-hemolysin may also be a positive charge. The α-hemolysin variant may also include a substitution at H144A of SEQ ID NO: 14. The α-hemolysin variant may also, in certain aspects, include one or more one or more glycine residues at residues 127-131 of SEQ ID NO: 14, such as a series of glycine residues that span the entire length of residues 127 through 131 of SEQ ID NO: 14.

In certain example aspects, the α-hemolysin variant includes an amino acid sequence having at least one of the substitutions described herein, while the sequence of the α-hemolysin variant has at least 80%, 90%, 95%, 98%, or more sequence identity to the amino acid sequence set forth as SEQ ID NO: 14. In certain example aspects, the α-hemolysin variant includes an amino acid sequence having at least 80%, 90%, 95%, 98%, or more sequence identity to the amino acid sequence set forth as SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13.

In certain example aspects, the alpha-hemolysin variant may include a substitution corresponding to H35G+V149K of SEQ ID NO: 14. Additionally or alternatively, the alpha-hemolysin variant may include a substitution corresponding to V149K+E287R+H35G of SEQ ID NO: 14. Additionally or alternatively, the alpha-hemolysin variant may include a substitution corresponding to V149K+E287R of SEQ ID NO: 14. Additionally or alternatively, the alpha-hemolysin variant may include a substitution corresponding to T109K+H35G of SEQ ID NO: 14. Additionally or alternatively, the alpha-hemolysin variant may include a substitution corresponding to P151K+H35G of SEQ ID NO: 14. Additionally or alternatively, the alpha-hemolysin variant may include a substitution corresponding to V149K+P151K+H35G of SEQ ID NO: 14. Additionally or alternatively, the alpha-hemolysin variant may include a substitution corresponding to T109K+V149K+H35G of SEQ ID NO: 14. Additionally or alternatively, the alpha-hemolysin variant may include a substitution at a position corresponding to V149K+K147N+E111N+127-131G+M113A+H35G of SEQ ID NO: 14. Additionally or alternatively, the alpha-hemolysin variant may include a substitution corresponding to V149K+K147N+E111N+127-131G+M113A of SEQ ID NO: 14. Additionally or alternatively, the alpha-hemolysin variant may include a substitution corresponding to T109K+V149K+P151K+H35G. In certain example aspects, any such combinations may also include a substitution at H144A of SEQ ID NO: 14.

In certain example aspects, the amino acid substitution described herein allows the addition of heterologous molecules, such as polyethylene glycol (PEG). In certain example aspects, the a-HL variant has one or more post-translational modifications. In certain example aspects, the substitution is a non-native amino acid that is basic or positively charged at a pH from about 5 to about 8.5.

In certain example aspects, the alpha-hemolysin variant described herein is bound to a DNA polymerase, such as via a covalent bond. For example, the alpha-hemolysin variant is bound to the DNA polymerase via a SpyTag/SpyCatcher linkage. In certain example aspects, the alpha-hemolysin variant is bound to the DNA polymerase via an isopeptide bond.

In certain example aspects, provided is a heptameric nanopore assembly. The assembly, for example, includes at least one or more of the alpha-hemolysin variants described herein. For example, the heptameric nanopore assembly may include one or more alpha-hemolysin molecules having a substitution at V149K, E287R, H35G, T109K, P151K, K147N, E111N, M113A, or combinations thereof of SEQ ID NO: 14, such as described herein.

In certain example aspects, provided is a heteromeric pore assembly including a mutant αHL polypeptide (M), e.g., a pore assembly which contains a wild type (WT) staphylococcal αHL polypeptide and a mutant αHL polypeptide in which an amino acid variant (as provided for herein) of the mutant αHL polypeptide occupies a position in a transmembrane channel of the pore structure. For example, the ratio of WT and variant αHL polypeptides is expressed by the formula $WT_{7-n}M_n$, where n is 1, 2, 3, 4, 5, 6, or 7. In certain aspects, the ratio of αHL polypeptides in the heteroheptamer is $WT_{7-n}M_n$. In other aspects, the ratio is $WT_6M_1$. Homomeric pores in which each subunit of the heptomer is a mutated αHL polypeptide (i.e., where n=7) are also encompassed by the disclosure provided herein.

The nanopore protein assemblies described herein, for example, can have an altered time to thread (TTT) relative to a pore complex consisting of native (wild type) alpha-hemolysin. For example, the TTT may be decreased, such as by about 10%, 20%, 30%, 40%, 50%, 60%, 70%, 80% or more as compared to a heptameric nanopore assembly including native (wild type) alpha-hemolysins.

In certain example aspects, also provided are nucleic acids encoding any of the alpha hemolysin variants described herein. For example, the nucleic acid sequence can be derived from *Staphylococcus aureus* (SEQ ID NO: 1). Also provided, in certain example aspects, are vectors that include an any such nucleic acids encoding any one of the hemolysin variants described herein. Also provided is a host cell that is transformed with the vector.

In certain example aspects, provided is a method of producing an alpha-hemolysin variant as descried herein. The method includes, for example, the steps of culturing a host cell including the vector in a suitable culture medium under suitable conditions to produce alpha-hemolysin variant. The variant is then obtained from the culture using methods known in the art.

In certain example aspects, provided is a method of detecting a target molecule. The method includes, for example, providing a chip comprising a nanopore assembly as described herein in a membrane that is disposed adjacent or in proximity to a sensing electrode. The method then includes directing a nucleic acid molecule through the nanopore. The nucleic acid molecule is associated with a reporter molecule and includes an address region and a probe region. The reporter molecule is associated with the nucleic acid molecule at the probe region and is coupled to a target molecule. The method further involves sequencing the address region while said nucleic acid molecule is directed through said nanopore to determine a nucleic acid sequence of said address region. The target molecule is identified, with the aid of a computer processor, based upon a nucleic acid sequence of the determined address region determined.

Other objects, features, and advantages of the present invention will become apparent from the following detailed description. It should be understood, however, that the detailed description and specific examples, while indicating preferred embodiments of the invention, are given by way of illustration only, since various changes and modifications within the scope and spirit of the invention will become apparent to one skilled in the art from this detailed description.

BRIEF DESCRIPTION OF THE DRAWINGS

FIG. 2 represents an analog to digital converter (ADC) value for our AC coupled system, which gives rise to an ADC value for open channel when the applied bias is positive (175 ADC units) and when the applied bias is negative (45 ADC units). When a tagged nucleotide is threaded into the pore, the ADC value during the application of positive bias decreases from the open channel level to 145 ADC units. Several examples of this are shown from 1020 to 1040s in the expanded lower panel of FIG. 2. When the applied bias is negative, the tagged nucleotide exits the pore, which is why the negative open channel level is not significantly reduced. In order to calculate the threading rate, a distribution of the times required in each positive bias period for the ADC value to reach a threaded level is counted for cycles whose immediately prior cycle ended at a threaded ADC value. This histogram is then fit to a standard single exponential function, whose decay rate is the threading rate.

DETAILED DESCRIPTION

Figure 1:
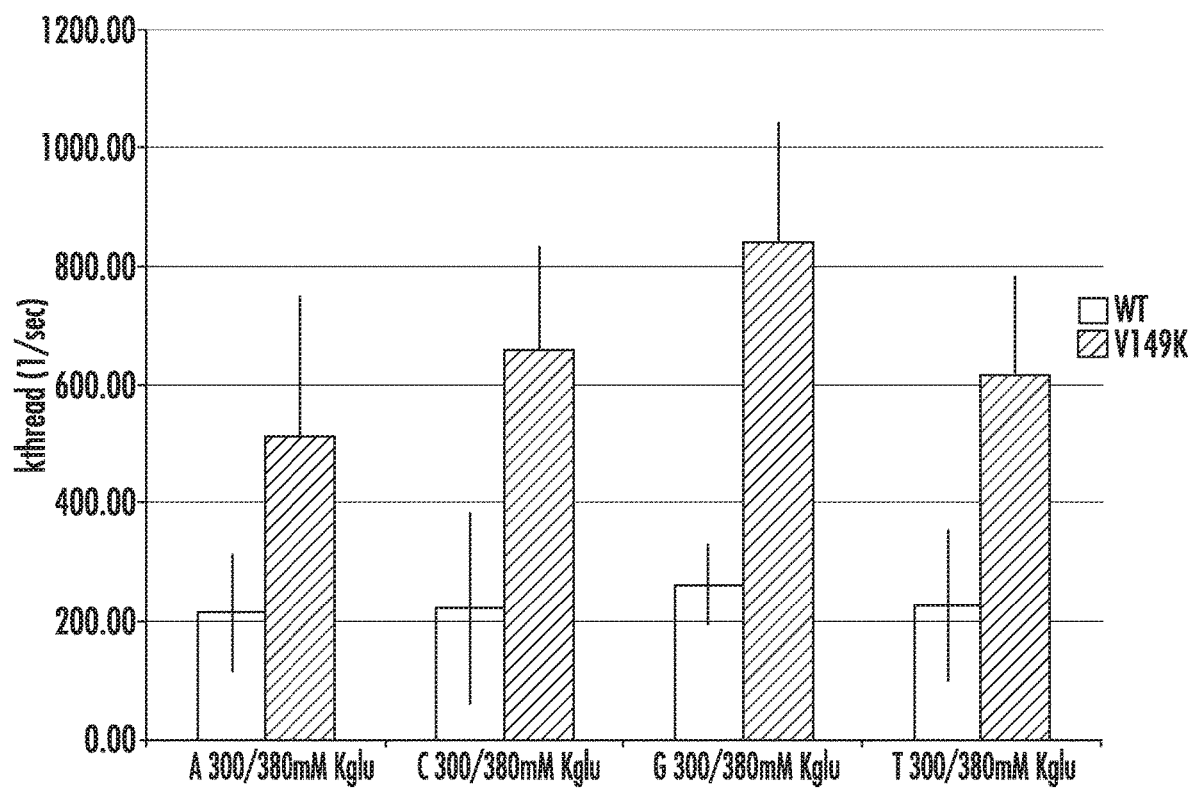
FIG. 1 is a graph showing the time-to-thread for control heptameric nanopores as compared to heptameric nanopores including one alpha-hemolysin/phi29 DNA Polymerase conjugate and six alpha-hemolysin variants, each variant having substitutions at H35G+V149K+H144A (i.e., a 1:6 ratio), as set forth in SEQ ID NO: 4. The control nanopores (labeled "WT") include a 1:6 ratio of alpha-hemolysin/phi29 DNA Polymerase conjugate to six wild-type alpha-hemolysins. These data are combined from many pores which were capturing the tagged nucleotides indicating the pore had both a polymerase and a template DNA molecule. As shown for each tag (corresponding to A, C, G, T), the threading rate for a nanopore including the variant alpha hemolysin was significantly increased compared to the control nanopore, thus evidencing an improved (decreased) time-to-thread. In the case of the C-nucleotide tag the threading rate increased from a mean value of 221.62 $s^{-1}$ (standard deviation 13.6 $s^{-1}$) to 663.15 (standard deviation 172 $s^{-1}$). Other nucleotide tags showed similar increases as shown in FIG. 1.

The invention will now be described in detail by way of reference only using the following definitions and examples. All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this invention. Although any methods and materials similar or equivalent to those described herein can be used in the practice or testing of the present invention, the preferred methods and materials are described. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

Numeric ranges are inclusive of the numbers defining the range. The term about is used herein to mean plus or minus ten percent (10%) of a value. For example, "about 100" refers to any number between 90 and 110.

Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention, which can be had by reference to the specification as a whole. Accordingly, the terms defined immediately below are more fully defined by reference to the specification as a whole.

DEFINITIONS

Alpha-hemolysin: As used herein, "alpha-hemolysin," "α-hemolysin," "a-HL" and "α-HL" are used interchangeably and refer to the monomeric protein that self-assembles into a heptameric water-filled transmembrane channel (i.e., nanopore). Depending on context, the term may also refer to the transmembrane channel formed by seven monomeric proteins.

Amino acid: As used herein, the term "amino acid," in its broadest sense, refers to any compound and/or substance that can be incorporated into a polypeptide chain. In some embodiments, an amino acid has the general structure $H_2N$—C(H)(R)—COOH. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" or "non-natural amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, and/or substitution with other chemical without adversely affecting their activity. Amino acids may participate in a disulfide bond. The term "amino acid" is used interchangeably with "amino acid residue," and may refer to a free amino acid and/or to an amino acid residue of a peptide. It will be apparent from the context in which the term is used whether it refers to a free amino acid or a residue of a peptide. It should be noted that all amino acid residue sequences are represented herein by formulae whose left and right orientation is in the conventional direction of amino-terminus to carboxy-terminus.

Base Pair (bp): As used herein, base pair refers to a partnership of adenine (A) with thymine (T), adenine (A) with uracil (U) or of cytosine (C) with guanine (G) in a double stranded nucleic acid.

Complementary: As used herein, the term "complementary" refers to the broad concept of sequence complementarity between regions of two polynucleotide strands or between two nucleotides through base-pairing. It is known that an adenine nucleotide is capable of forming specific hydrogen bonds ("base pairing") with a nucleotide which is thymine or uracil. Similarly, it is known that a cytosine nucleotide is capable of base pairing with a guanine nucleotide.

Expression cassette: An "expression cassette" or "expression vector" is a nucleic acid construct generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter.

Heterologous: A "heterologous" nucleic acid construct or sequence has a portion of the sequence which is not native to the cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, transformation, microinjection, electroporation, or the like. A "heterologous" nucleic acid construct may contain a control sequence/DNA coding sequence combination that is the same as, or different from a control sequence/DNA coding sequence combination found in the native cell.

Host cell: By the term "host cell" is meant a cell that contains a vector and supports the replication, and/or transcription or transcription and translation (expression) of the expression construct. Host cells for use in the present invention can be prokaryotic cells, such as *E. coli* or *Bacillus subtilus*, or eukaryotic cells such as yeast, plant, insect, amphibian, or mammalian cells. In general, host cells are prokaryotic, e.g., *E. coli*.

Isolated: An "isolated" molecule is a nucleic acid molecule that is separated from at least one other molecule with which it is ordinarily associated, for example, in its natural environment. An isolated nucleic acid molecule includes a nucleic acid molecule contained in cells that ordinarily express the nucleic acid molecule, but the nucleic acid molecule is present extrachromasomally or at a chromosomal location that is different from its natural chromosomal location.

Modified alpha-hemolysin: As used herein, the term "modified alpha-hemolysin" refers to an alpha-hemolysin originated from another (i.e., parental) alpha-hemolysin and contains one or more amino acid alterations (e.g., amino acid substitution, deletion, or insertion) compared to the parental alpha-hemolysin. In some embodiments, a modified alpha-hemolysin of the invention is originated or modified from a naturally-occurring or wild-type alpha-hemolysin. In some embodiments, a modified alpha-hemolysin of the invention is originated or modified from a recombinant or engineered alpha-hemolysin including, but not limited to, chimeric alpha-hemolysin, fusion alpha-hemolysin or another modified alpha-hemolysin. Typically, a modified alpha-hemolysin has at least one changed phenotype compared to the parental alpha-hemolysin.

Mutation: As used herein, the term "mutation" refers to a change introduced into a parental sequence, including, but not limited to, substitutions, insertions, deletions (including truncations). The consequences of a mutation include, but are not limited to, the creation of a new character, property, function, phenotype or trait not found in the protein encoded by the parental sequence.

Nanopore: The term "nanopore," as used herein, generally refers to a pore, channel or passage formed or otherwise provided in a membrane. A membrane may be an organic membrane, such as a lipid bilayer, or a synthetic membrane, such as a membrane formed of a polymeric material. The membrane may be a polymeric material. The nanopore may be disposed adjacent or in proximity to a sensing circuit or an electrode coupled to a sensing circuit, such as, for example, a complementary metal-oxide semiconductor (CMOS) or field effect transistor (FET) circuit. In some examples, a nanopore has a characteristic width or diameter on the order of 0.1 nanometers (nm) to about 1000 nm. Some nanopores are proteins. Alpha-hemolysin is an example of a protein nanopore.

Nucleic Acid Molecule: The term "nucleic acid molecule" includes RNA, DNA and cDNA molecules. It will be understood that, as a result of the degeneracy of the genetic code, a multitude of nucleotide sequences encoding a given protein such as alpha-hemolysin and/or variants thereof may be produced. The present invention contemplates every possible variant nucleotide sequence, encoding variant alpha-hemolysin, all of which are possible given the degeneracy of the genetic code.

Promoter: As used herein, the term "promoter" refers to a nucleic acid sequence that functions to direct transcription of a downstream gene. The promoter will generally be appropriate to the host cell in which the target gene is being expressed. The promoter together with other transcriptional and translational regulatory nucleic acid sequences (also termed "control sequences") are necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

Purified: As used herein, "purified" means that a molecule is present in a sample at a concentration of at least 95% by weight, or at least 98% by weight of the sample in which it is contained.

Purifying: As used herein, the term "purifying" generally refers to subjecting transgenic nucleic acid or protein containing cells to biochemical purification and/or column chromatography.

Tag: As used herein, the term "tag" refers to a detectable moiety that may be atoms or molecules, or a collection of atoms or molecules. A tag may provide an optical, electrochemical, magnetic, or electrostatic (e.g., inductive, capacitive) signature, which signature may be detected with the aid of a nanopore. Typically, when a nucleotide is attached to the tag it is called a "Tagged Nucleotide." The tag may be attached to the nucleotide via the phosphate moiety.

Time-To-Thread: The term "time to thread" or "TTT" means the time it takes the polymerase-tag complex or a nucleic acid strand to thread the tag into the barrel of the nanopore.

Variant: As used herein, the term "variant" refers to a modified protein which displays altered characteristics when compared to the parental protein, e.g., altered ionic conductance.

Variant hemolysin: The term "variant hemolysin gene" or "variant hemolysin" means, respectively, that the nucleic acid sequence of the alpha-hemolysin gene from *Staphylococcus aureus* has been altered by removing, adding, and/or manipulating the coding sequence or the amino acid sequence of the expressed protein has been modified consistent with the invention described herein.

Vector: As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

Wild-type: As used herein, the term "wild-type" refers to a gene or gene product which has the characteristics of that gene or gene product when isolated from a naturally-occurring source.

Percent homology: The term "% homology" is used interchangeably herein with the term "% identity" herein and refers to the level of nucleic acid or amino acid sequence identity between the nucleic acid sequence that encodes any one of the inventive polypeptides or the inventive polypeptide's amino acid sequence, when aligned using a sequence alignment program. For example, as used herein, 80% homology means the same thing as 80% sequence identity determined by a defined algorithm, and accordingly a homologue of a given sequence has greater than 80% sequence identity over a length of the given sequence. Exemplary levels of sequence identity include, but are not limited to, 80, 85, 90, 95, 98% or more sequence identity to a given sequence, e.g., the coding sequence for any one of the inventive polypeptides, as described herein.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet. See also, Altschul, et al., 1990 and Altschul, et al., 1997.

Sequence searches are typically carried out using the BLASTN program when evaluating a given nucleic acid sequence relative to nucleic acid sequences in the GenBank DNA Sequences and other public databases. The BLASTX program is preferred for searching nucleic acid sequences that have been translated in all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62 matrix. (See, e.g., Altschul, S. F., et al., Nucleic Acids Res. 25:3389-3402, 1997.)

A preferred alignment of selected sequences in order to determine "% identity" between two or more sequences, is performed using for example, the CLUSTAL-W program in MacVector version 13.0.7, operated with default parameters, including an open gap penalty of 10.0, an extended gap penalty of 0.1, and a BLOSUM 30 similarity matrix.

Nomenclature

In the present description and claims, the conventional one-letter and three-letter codes for amino acid residues are used.

For ease of reference, variants of the application are described by use of the following nomenclature: Original amino acid(s); position(s); substituted amino acid(s). According to this nomenclature, for instance, the substitution of a valine by a lysine in position 149 is shown as:

Val149Lys or V149K

Multiple mutations are separated by plus signs, such as:

His35Gly+Val149Lys or H35G+V149K representing mutations in positions 35 and 149 substituting glycine for histidine and lysine for valine, respectively.

Spans of amino acid substitutions are represented by a dash, such as a span of glycine residues from residue 127 to 131 being: 127-131Gly or 127-133G.

Site-Directed Mutagenesis of Alpha-Hemolysin

*Staphylococcus aureus* alpha hemolysin wild type sequences are provided herein (SEQ ID NO:1, nucleic acid coding region; SEQ ID NO:14, protein coding region) and available elsewhere (National Center for Bioinformatics or GenBank Accession Numbers M90536 and AAA26598).

Point mutations may be introduced by any method known in the art. For example, a point mutation may be made using QuikChange Lightning 2 kit (Stategene/Agilent) following manufacturer's instructions.

Primers can be ordered from commercial companies, e.g., IDT DNA.

Alpha-Hemolysin Variants

The alpha-hemolysin variants provided herein include specific substitutions, or one or more combination of substitutions, that improve the time-to-thread in a nanopore-based, sequencing reaction. By improving the time-to-thread, high accuracy DNA sequencing can be achieved with fewer deletions in the determined sequence.

In certain example embodiments, the alpha-hemolysin variant provided herein includes one or more mutations at one or more of the locations of the amino acid sequence set forth as SEQ ID NO: 14. For example, any one of the residues identified in Table 1, or combinations thereof, may be mutated to form an alpha-hemolysin variant. In certain example embodiments, the alpha-hemolysin variant formed from muting one or more of the amino acids of SEQ ID NO:14 identified in Table 1 has 80%, 85%, 90%, 95%, 98% or more sequence identity to the sequence set forth as SEQ ID NO: 14. In certain example embodiments, the mutation results in the addition of a positive charge. For example, the mutation may result in a substitution of an amino acid residue identified in Table 1 to an arginine, lysine, histidine, asparagine, or other amino acid that can carry a positive charge.

In certain example embodiments, the mutation includes a particular substitution. For example, the variant may include an amino acid substitution of any one of V149K, E287R, H35G, T109K, P151K, K147N, E111N, M113A, or combinations thereof of SEQ ID NO: 14. In other example embodiments, the variant may include one or more these same substitutions, while the overall sequence can have up to 80%, 85%, 90%, 95%, 98% or more sequence identity to the amino acid sequence set forth as SEQ ID NO: 14. In certain example embodiments, one or more of the first 17 amino acids of SEQ ID NO: 14 mutated to either an A, N, K, or combinations thereof.

To improve nanopore stability, for example, any of the alpha-hemolysin variants described herein may also include an amino acid substitution at H144A of SEQ ID NO: 14. Additionally or alternatively, any of the variants may include a series of glycine residue substitutions spanning from residue 127 to residue 131 of the sequence set forth as SEQ ID NO: 14.

TABLE 1

Residues of mature alpha-hemolysin that can be mutated to form alpha-hemolysin variant.

| Position* | Residue |
|---|---|
| 1 | ALA |
| 2 | ASP |

TABLE 1-continued

Residues of mature alpha-hemolysin that can be mutated to form alpha-hemolysin variant.

| Position* | Residue |
|---|---|
| 3 | SER |
| 4 | ASP |
| 5 | ILE |
| 6 | ASN |
| 8 | LYS |
| 9 | THR |
| 10 | GLY |
| 11 | THR |
| 13 | ASP |
| 14 | ILE |
| 15 | GLY |
| 16 | SER |
| 17 | ASN |
| 18 | THR |
| 19 | THR |
| 20 | VAL |
| 21 | LYS |
| 22 | THR |
| 24 | ASP |
| 25 | LEU |
| 26 | VAL |
| 27 | THR |
| 28 | TYR |
| 29 | ASP |
| 30 | LYS |
| 31 | GLU |
| 32 | ASN |
| 33 | GLY |
| 35 | HIS |
| 36 | LYS |
| 37 | LYS |
| 40 | TYR |
| 44 | ASP |
| 45 | ASP |
| 46 | LYS |
| 47 | ASN |
| 48 | HIS |
| 49 | ASN |
| 50 | LYS |
| 51 | LYS |
| 56 | ARG |
| 62 | ALA |
| 64 | GLN |
| 65 | TYR |
| 66 | ARG |
| 67 | VAL |
| 68 | TYR |
| 69 | SER |
| 70 | GLU |
| 71 | GLU |
| 72 | GLY |
| 73 | ALA |
| 74 | ASN |
| 75 | LYS |
| 79 | ALA |
| 82 | SER |
| 83 | ALA |
| 85 | LYS |
| 87 | GLN |
| 89 | GLN |
| 90 | LEU |
| 91 | PRO |
| 92 | ASP |
| 93 | ASN |
| 94 | GLU |
| 95 | VAL |
| 97 | GLN |
| 102 | TYR |
| 103 | PRO |
| 104 | ARG |
| 105 | ASN |
| 106 | SER |
| 107 | ILE |
| 108 | ASP |
| 109 | THR |

TABLE 1-continued

Residues of mature alpha-hemolysin that can be mutated to form alpha-hemolysin variant.

| Position* | Residue |
|---|---|
| 110 | LYS |
| 111 | GLU |
| 112 | TYR |
| 113 | MET |
| 114 | SER |
| 115 | THR |
| 116 | LEU |
| 117 | THR |
| 118 | TYR |
| 120 | PHE |
| 121 | ASN |
| 122 | GLY |
| 123 | ASN |
| 124 | VAL |
| 125 | THR |
| 126 | GLY |
| 127 | ASP |
| 128 | ASP |
| 129 | THR |
| 130 | GLY |
| 131 | LYS |
| 132 | ILE |
| 134 | GLY |
| 135 | LEU |
| 136 | ILE |
| 137 | GLY |
| 138 | ALA |
| 139 | ASN |
| 140 | VAL |
| 141 | SER |
| 142 | ILE |
| 143 | GLY |
| 144 | HIS |
| 145 | THR |
| 146 | LEU |
| 147 | LYS |
| 148 | TYR |
| 149 | VAL |
| 150 | GLN |
| 151 | PRO |
| 152 | ASP |
| 153 | PHE |
| 154 | LYS |
| 155 | THR |
| 156 | ILE |
| 158 | GLU |
| 159 | SER |
| 160 | PRO |
| 161 | THR |
| 162 | ASP |
| 163 | LYS |
| 164 | LYS |
| 168 | LYS |
| 170 | ILE |
| 171 | PHE |
| 172 | ASN |
| 173 | ASN |
| 174 | MET |
| 175 | VAL |
| 176 | ASN |
| 177 | GLN |
| 178 | ASN |
| 179 | TRP |
| 180 | GLY |
| 181 | PRO |
| 182 | TYR |
| 183 | ASP |
| 184 | ARG |
| 185 | ASP |
| 186 | SER |
| 187 | TRP |
| 188 | ASN |
| 189 | PRO |
| 190 | VAL |
| 191 | TYR |
| 193 | ASN |
| 194 | GLN |
| 197 | MET |
| 198 | LYS |
| 199 | THR |
| 200 | ARG |
| 201 | ASN |
| 202 | GLY |
| 203 | SER |
| 204 | MET |
| 205 | LYS |
| 207 | ALA |
| 208 | ASP |
| 210 | PHE |
| 211 | LEU |
| 212 | ASP |
| 213 | PRO |
| 214 | ASN |
| 215 | LYS |
| 216 | ALA |
| 218 | SER |
| 221 | SER |
| 222 | SER |
| 224 | PHE |
| 225 | SER |
| 226 | PRO |
| 227 | ASP |
| 228 | PHE |
| 229 | ALA |
| 235 | ASP |
| 236 | ARG |
| 237 | LYS |
| 238 | ALA |
| 239 | SER |
| 240 | LYS |
| 241 | GLN |
| 244 | ASN |
| 246 | ASP |
| 250 | GLU |
| 252 | VAL |
| 253 | ARG |
| 255 | ASP |
| 257 | GLN |
| 259 | HIS |
| 260 | TRP |
| 261 | THR |
| 262 | SER |
| 263 | THR |
| 264 | ASN |
| 266 | LYS |
| 268 | THR |
| 269 | ASN |
| 270 | THR |
| 271 | LYS |
| 272 | ASP |
| 273 | LYS |
| 274 | TRP |
| 275 | THR |
| 276 | ASP |
| 277 | ARG |
| 278 | SER |
| 280 | GLU |
| 281 | ARG |
| 282 | TYR |
| 283 | LYS |
| 285 | ASP |
| 286 | TRP |
| 287 | GLU |
| 288 | LYS |
| 289 | GLU |
| 291 | MET |
| 292 | THR |
| 293 | ASN |

*Position corresponds to the specific amino acid position in SEQ ID NO: 14.

While the α-hemolysin variant can include various combinations of substitutions as described herein, in certain example embodiments the α-hemolysin variant includes particular combinations of substitutions. For example, an α-hemolysin variant may include the following combinations of amino acid substitutions of the sequence set forth as SEQ ID NO: 14:

H35G+V149K;
V149K+E287R+H35G;
V149K+E287R;
T109K+H35G;
P151K+H35G;
V149K+P151K+H35G;
T109K+V149K+H35G;
V149K+K147N+E111N+127-131G+M113A+H35G;
V149K+K147N+E111N+127-131G+M113A; or,
T109K+V149K+P151K+H35G.

Such combinations may also include, for example, a substitution at H144A of SEQ ID NO: 14 and/or a series of glycine residues at amino acids 127-131 of SEQ ID NO: 14. In certain example embodiments, the α-hemolysin variant includes an amino acid sequence having at least 80%, 90%, 95%, 98%, or more sequence identity to the amino acid sequence set forth as SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13, with the substitution(s) identified in each sequence, for example, being preserved in the variant.

So that the variants and WT alpha-hemolysin can be manipulated, in certain example embodiments any of the amino acid sequences described herein, such as those set forth as SEQ ID NO: 4-14, may also include a linker/TEV/HisTAG sequence at the C-terminal end having the sequence GLSAENLYFQGHHHHHH (SEQ ID NO: 16, where the TEV sequence is underlined). As those skilled in the art will appreciate, such a sequence allows for the purification of the variant.

Nanopore Assembly and Insertion

The methods described herein can use a nanopore having a polymerase attached to the nanopore. In certain example embodiments, it is desirable to have one and only one polymerase per nanopore (e.g., so that only one nucleic acid molecule is sequenced at each nanopore). However, many nanopores, including alpha-hemolysin (aHL), can be multimeric proteins having a plurality of subunits (e.g., 7 subunits for aHL). The subunits can be identical copies of the same polypeptide. Provided herein are multimeric proteins (e.g., nanopores) having a defined ratio of modified subunits (e.g., a-HL variants) to un-modified subunits (e.g., a-HL).

Also provided herein are methods for producing multimeric proteins (e.g., nanopores or nanopore assemblies) having a defined ratio of modified subunits to un-modified subunits. For example, the nanopore assembly may include any of the alpha-hemolysin variants described herein. A heptameric nanopore assembly, for example, may include one or more alpha-hemolysin subunits having an amino acidic sequence corresponding to a substitution of any one of V149K, E287R, H35G, T109K, P151K, K147N, E111N, M113A, or combinations thereof of SEQ ID NO: 14. In certain example embodiments, one or more of the subunits may include a specific combination of substitutions as described herein. Any of the variants used in the nanopore assembly, such as in a heptameric assembly, may also include an H144A substitution of SEQ ID NO: 14.

With reference to FIG. 27 of WO2014/074727, a method for assembling a protein having a plurality of subunits includes providing a plurality of first subunits 2705 and providing a plurality of second subunits 2710, where the second subunits are modified when compared with the first subunits. In some cases, the first subunits are wild-type (e.g., purified from native sources or produced recombinantly). The second subunits can be modified in any suitable way. In some cases, the second subunits have a protein (e.g., a polymerase) attached (e.g., as a fusion protein).

In certain example embodiments, the modified subunits can comprise a chemically reactive moiety (e.g., an azide or an alkyne group suitable for forming a linkage). In some cases, the method further comprises performing a reaction (e.g., a Click chemistry cycloaddition) to attach an entity (e.g., a polymerase) to the chemically reactive moiety.

In certain example embodiments, the method can further include contacting the first subunits with the second subunits 2715 in a first ratio to form a plurality of proteins 2720 having the first subunits and the second subunits. For example, one part modified aHL subunits having a reactive group suitable for attaching a polymerase can be mixed with six parts wild-type aHL subunits (i.e., with the first ratio being 1:6). The plurality of proteins can have a plurality of ratios of the first subunits to the second subunits. For example, the mixed subunits can form several nanopores having a distribution of stoichiometries of modified to un-modified subunits (e.g., 1:6, 2:5, 3:4).

In certain example embodiments, the proteins are formed by simply mixing the subunits. In the case of aHL nanopores for example, a detergent (e.g., deoxycholic acid) can trigger the aHL monomer to adopt the pore conformation. The nanopores can also be formed, for example, using a lipid (e.g., 1,2-diphytanoyl-sn-glycero-3-phosphocholine (DPhPC) or 1,2-di-0-phytanyl-sn-glycero-3-phosphocholine (DoPhPC)) and moderate temperature (e.g., less than about 100° C.). In some cases, mixing DPhPC with a buffer solution creates large multi-lamellar vesicles (LMV), and adding aHL subunits to this solution and incubating the mixture at 40° C. for 30 minutes results in pore formation.

If two different types of subunits are used (e.g., the natural wild type protein and a second aHL monomer which can contain a single point mutation), the resulting proteins can have a mixed stoichiometry (e.g., of the wild type and mutant proteins). The stoichiometry of these proteins can, in certain example embodiments, follow a formula which is dependent upon the ratio of the concentrations of the two proteins used in the pore forming reaction. This formula is as follows:

$$100P_m = 100[n!/m!(n-m)!] \cdot f_{mut}^m \cdot f_{wt}^{n-m}, \text{ where}$$

$P_m$=probability of a pore having m number of mutant subunits
n=total number of subunits (e.g., 7 for aHL)
m=number of "mutant" subunits
$f_{mut}$=fraction or ratio of mutant subunits mixed together
$f_{wt}$=fraction or ratio of wild-type subunits mixed together The method can further comprise fractionating the plurality of proteins to enrich proteins that have a second ratio of the first subunits to the second subunits 2725. For example, nanopore proteins can be isolated that have one and only one modified subunit (e.g., a second ratio of 1:6). However, any second ratio is suitable. A distribution of second ratios can also be fractionated such as enriching proteins that have either one or two modified subunits. The total number of subunits forming the protein is not always 7 (e.g., a different nanopore can be used or an alpha-hemolysin nanopore can form having six subunits) as depicted in FIG. 27 of WO2014/074727. In some cases, proteins having only one modified subunit are enriched. In such cases, the second ratio is 1 second subunit per (n−1) first subunits where n is the number of subunits comprising the protein.

The first ratio can be the same as the second ratio, however this is not required. In some cases, proteins having mutated monomers can form less efficiently than those not having mutated subunits. If this is the case, the first ratio can be greater than the second ratio (e.g., if a second ratio of 1 mutated to 6 non-mutated subunits are desired in a nanopore, forming a suitable number of 1:6 proteins may require mixing the subunits at a ratio greater than 1:6).

Proteins having different second ratios of subunits can behave differently (e.g., have different retention times) in a separation. In certain example embodiments, the proteins are fractionated using chromatography, such as ion exchange chromatography or affinity chromatography. Since the first and second subunits can be identical apart from the modification, the number of modifications on the protein can serve as a basis for separation. In some cases, either the first or second subunits have a purification tag (e.g., in addition to the modification) to allow or improve the efficiency of the fractionation. In some cases, a poly-histidine tag (His-tag), a streptavidin tag (Strep-tag), or other peptide tag is used. In some instances, the first and second subunits each comprise different tags and the fractionation step fractionates on the basis of each tag. In the case of a His-tag, a charge is created on the tag at low pH (Histidine residues become positively charged below the pKa of the side chain). With a significant difference in charge on one of the aHL molecules compared to the others, ion exchange chromatography can be used to separate the oligomers which have 0, 1, 2, 3, 4, 5, 6, or 7 of the "charge-tagged" aHL subunits. In principle, this charge tag can be a string of any amino acids which carry a uniform charge. FIG. 28 and FIG. 29 show examples of fractionation of nanopores based on a His-tag. FIG. 28 shows a plot of ultraviolet absorbance at 280 nanometers, ultraviolet absorbance at 260 nanometers, and conductivity. The peaks correspond to nanopores with various ratios of modified and unmodified subunits. FIG. 29 of WO2014/074727 shows fractionation of aHL nanopores and mutants thereof using both His-tag and Strep-tags.

In certain example embodiments, an entity (e.g., a polymerase) is attached to the protein following fractionation. The protein can be a nanopore and the entity can be a polymerase. In some instances, the method further comprises inserting the proteins having the second ratio subunits into a bilayer.

In certain example embodiments, a nanopore can comprise a plurality of subunits. As described herein, a polymerase can be attached to one of the subunits and at least one and less than all of the subunits comprise a first purification tag. In some example embodiments, the nanopore is alpha-hemolysin or a variant thereof. In some instances, all of the subunits comprise a first purification tag or a second purification tag. The first purification tag can, for example, be a poly-histidine tag (e.g., on the subunit having the polymerase attached).

Polymerase Attached to Nanopore

In certain example embodiments, a polymerase (e.g., DNA polymerase) is attached to and/or is located in proximity to the nanopore. Any DNA polymerase capable of synthesizing DNA during a DNA synthesis reaction may be used in accordance with the methods and compositions described herein. Example DNA polymerases include, but are not limited to, phi29 (Bacillus bacteriophage φ29), pol6 (Clostridium phage phiCPV4; GenBank: AFH27113.1) or pol7 (*Actinomyces* phage Av-1; GenBank: ABR67671.1). In certain example embodiments, attached to the nanopore assembly is a DNA-manipulating or modifying enzyme, such as a ligase, nuclease, phosphatase, kinase, transferase, or topoisomerase.

In certain example embodiments, the polymerase is a polymerase variant. For example, the polymerase variant may include any of the polymerase variants identified in U.S. patent application Ser. No. 15/012,317 (the "317 Application"). Such variants include, for example, one or more amino acid substitutions at H223A, N224Y/L, Y225L/T/I/F/A, H227P, I295 W/F/M/E, Y342L/F, T343N/F, I357G/L/Q/H/W/M/A/E/Y/P, S360G, L361M/W/V, I363V, S365Q/W/M/A/G, S366A/L, Y367L/E/M/P/N, P368G, D417P, E475D, Y476V, F478L, K518Q, H527 W/R/L, T529M/F, M531H/Y/A/K/R/W/T/L/V, N535L/Y/M/K/I, G539Y/F, P542E/S, N545K/D/S/L/R, Q546 W/F, A547M/Y/W/F/V/S, L549Q/Y/H/G/R, I550A/W/T/G/F/S, N552L/M/S, G553S/T, F558P/T, A596S, G603T, A610T/E, V615A/T, Y622A/M, C623G/S/Y, D624F, I628Y/V/F, Y629 W/H/M, R632L/C, N635D, M641 L/Y, A643L, I644H/M/Y, T647G/A/E/K/S, I648K/R/V/N/T, T651Y/F/M, I652Q/G/S/N/F/T, K655G/F/E/N, W656E, D657R/P/A, V658L, H660A/Y, F662I/L, L690M, or combinations thereof of SEQ ID NO: 15 (which corresponds to SEQ ID NO: 2 of the '317 Application). In certain example embodiments, the polymerase includes one or more such substitutions and has 80%, 90%, 95%, 98% or more sequence identity to the amino acid sequence set forth as SEQ ID NO: 15. As described in the '317 Application, the polymerase variant has altered enzyme activity, fidelity, processivity, elongation rate, sequencing accuracy, long continuous read capability, stability, or solubility relative to the parental polymerase.

The polymerase can be attached to the nanopore in any suitable way. A polymerase, for example, can be attached to the nanopore assembly in any suitable way known in the art. See, for example, PCT/US2013/068967 (published as WO2014/074727; Genia Technologies), PCT/US2005/009702 (published as WO2006/028508), and PCT/US2011/065640 (published as WO2012/083249; Columbia Univ). In certain example embodiments, the polymerase is attached to the nanopore (e.g., hemolysin) protein monomer and then the full nanopore heptamer is assembled (e.g., in a ratio of one monomer with an attached polymerase to 6 nanopore (e.g., hemolysin) monomers without an attached polymerase). The nanopore heptamer can then be inserted into the membrane.

Another method for attaching a polymerase to a nanopore involves attaching a linker molecule to a hemolysin monomer or mutating a hemolysin monomer to have an attachment site and then assembling the full nanopore heptamer (e.g., at a ratio of one monomer with linker and/or attachment site to 6 hemolysin monomers with no linker and/or attachment site). A polymerase can then be attached to the attachment site or attachment linker (e.g., in bulk, before inserting into the membrane). The polymerase can also be attached to the attachment site or attachment linker after the (e.g., heptamer) nanopore is formed in the membrane. In some cases, a plurality of nanopore-polymerase pairs are inserted into a plurality of membranes (e.g., disposed over the wells and/or electrodes) of the biochip. In some instances, the attachment of the polymerase to the nanopore complex occurs on the biochip above each electrode.

The polymerase can be attached to the nanopore with any suitable chemistry (e.g., covalent bond and/or linker). In some cases, the polymerase is attached to the nanopore with molecular staples. In some instances, molecular staples comprise three amino acid sequences (denoted linkers A, B and C). Linker A can extend from a hemolysin monomer, Linker B can extend from the polymerase, and Linker C then can bind Linkers A and B (e.g., by wrapping around both Linkers A and B) and thus the polymerase to the nanopore. Linker C can also be constructed to be part of Linker A or Linker B, thus reducing the number of linker molecules.

In certain example embodiments, the polymerase is linked to the nanopore using Solulink™ chemistry. Solulink™ can be a reaction between HyNic (6-hydrazino-nicotinic acid, an aromatic hydrazine) and 4FB (4-formylbenzoate, an aromatic aldehyde). In some instances, the polymerase is linked to the nanopore using Click chemistry (available from LifeTechnologies for example). In some cases, zinc finger mutations are introduced into the hemolysin molecule and then a molecule is used (e.g., a DNA intermediate molecule) to link the polymerase to the zinc finger sites on the hemolysin.

Additionally or alternatively, the SpyTag/SpyCatcher system, which spontaneously forms covalent isopeptide linkages under physiological conditions, may be used to join an alpha-hemolysin monomer to the polymerase. See, for example, Li et al, J Mol Biol. 2014 Jan. 23; 426(2):309-17. For example, an alpha-hemolysin protein can be expressed having a SpyTag domain. Further, the DNA polymerase to be joined to the alpha-hemolysin may be separately expressed as fusion protein having a SpyCatcher domain. By mixing the alpha-hemolysin/SpyTag fusion protein with the DNA Polymerase/SpyCatcher protein, the SpyTag and Spy-Catcher proteins interact to form the alpha-hemolysin monomer that is linked to a DNA polymerase via a covalent isopeptide linkage.

In certain example embodiments, the polymerase may be attached to a nanopore monomer before the nanopore monomer is incorporated into a nanopore assembly. For example, following expression and purification of the alpha-hemolysin/SpyTag fusion protein, the purified alpha-hemolysin/SpyTag fusion protein is mixed with purified polymerase/SpyCatcher fusion protein, thus allowing the SpyTag and SpyCatcher proteins bind each other to form an alpha-hemolysin/polymerase monomer. The monomer can then be incorporated into the nanopore assembly as described herein to form a heptameric assembly.

In certain example embodiments, the polymerase is attached to the nanopore assembly after formation of the nanopore assembly. For example, following expression and purification of the alpha-hemolysin/SpyTag fusion protein, the fusion protein is incorporated into the nanopore assembly to form the heptameric nanopore assembly. The polymerase/SpyCatcher fusion protein is then mixed with the heptameric assembly, thus allowing the SpyTag and SpyCatcher proteins bind each other, which in turn results in binding of the polymerase to the nanopore assembly.

Because of the nature of nanopore-based sequencing reaction, those skilled in the art will appreciate that it is beneficial to have only a single polymerase associated with each nanopore assembly (rather than multiple polymerases). To achieve such assemblies, the nanopore assembly may be configured, for example, to have only a single SpyTag, which therefore allows the attachment of a single polymerase/SpyCatcher.

In the case of alpha-hemolysin, for example, mixing the alpha-hemolysin/SpyTag proteins with additional alpha-hemolysin proteins results in heptamers having 0, 1, 2, 3, 4, 5, 6, or 7 alpha-hemolysin/SpyTag subunits. Yet because of the different number of SpyTag sequences (0, 1, 2, 3, 4, 5, 6, or 7) associated with each heptamer, the heptamers have different charges. Hence, in certain example embodiments, the heptamers can be separated by methods known in the art, such as via elution with cation exchange chromatography. The eluted fractions can then be examined to determine which fraction includes an assembly with a single SpyTag. The fraction with a single SpyTag can then be used to attach a single polymerase to each assembly, thereby creating a nanopore assemblies with a single polymerase attached thereto.

While a variety of methods may be suitable for determining which heptamer fraction contains a single SpyTag (and that is hence capable of binding a only single polymerase/SpyCatcher fusion protein per heptamer), in certain example embodiments the different heptamer fraction can be separated based on molecular weight, such as via SDS-PAGE. A reagent can then be used to confirm the presence of SpyTag associated with each fraction. For example, a SpyCatcher-GFP (green fluorescent protein) can be added to the fractions before separation via SDS-PAGE.

Because heptamers with fewer number of SpyTags are smaller than the heptamers with greater number of SpyTags, the fraction with a single SpyTag can be identified, as evidenced by the furthest band migration and the presence of GFP fluorescence in the SDS-PAGE gel corresponding to the band. For example, a fraction containing seven alpha-hemolysin monomers and zero SpyTag fusion proteins will migrate the furthest, but will not fluoresce when mixed with SpyCatcher-GFP because of the absence of the SpyTag bound to the heptamers. The fraction containing a single SpyTag, however, will both migrate the next furthest (compared to other fluorescent bands) and will fluoresce, thereby allowing identification of the fraction with a single SpyTag bound to the heptamer. Following identification of the fraction with a single SpyTag bound to the heptamer, the polymerase/SpyCatcher fusion protein can then be added to this fraction, thereby linking the polymerase to the nanopore assembly.

By using the methods and compositions described herein, a nanopore assembly tethered to a single DNA polymerase—and including one or more of the alpha hemolysin variants as described herein—can be achieved. For example, the heptameric nanopore may include one alpha-hemolysin variant having a substitution corresponding to any one of V149K, E287R, H35G, T109K, P151K, K147N, E111N, M113A, or combinations thereof of SEQ ID NO: 14, five mature wild type alpha hemolysin monomers, and a seventh alpha-hemolysin monomer that is fused to a polymerase (for a total of seven subunits of the heptamer). In certain example embodiments, the nanopore heptamer assembly may include 1, 2, 3, 4, 5, 6, or 7 of the variants described herein, with one of the subunits being attached to a polymerase as described herein.

Apparatus Set-Up

The nanopore may be formed or otherwise embedded in a membrane disposed adjacent to a sensing electrode of a sensing circuit, such as an integrated circuit. The integrated circuit may be an application specific integrated circuit (ASIC). In some examples, the integrated circuit is a field effect transistor or a complementary metal-oxide semiconductor (CMOS). The sensing circuit may be situated in a chip or other device having the nanopore, or off of the chip or device, such as in an off-chip configuration. The semiconductor can be any semiconductor, including, without limitation, Group IV (e.g., silicon) and Group III-V semiconductors (e.g., gallium arsenide). See, for example, WO 2013/123450, for the apparatus and device set-up for sensing a nucleotide or tag.

Pore based sensors (e.g., biochips) can be used for electro-interrogation of single molecules. A pore based sensor can include a nanopore of the present disclosure formed in a membrane that is disposed adjacent or in proximity to a sensing electrode. The sensor can include a counter electrode. The membrane includes a trans side (i.e., side facing the sensing electrode) and a cis side (i.e., side facing the counter electrode).

In certain example embodiments, a nanopore including one or more of the alpha-hemolysin variants described herein, will have an altered time to thread relative to a nanopore including wild-type alpha-hemolysin (i.e., a nanopore without any of the substitutions described herein). For example, the time for a tag to thread through the pore (the time-to-thread or TTT) may be decreased. In certain example embodiments, the TTT for a nanopore comprising one or more of the variants described herein may be decreased by about 10%, 20%, 30%, 40%, 50%, 60%, 70%, 80% or more as compared to a heptameric nanopore assembly consisting of native alpha-hemolysin.

In the experimental disclosure that follows, the following abbreviations apply: eq (equivalents); M (Molar); µM (micromolar); N (Normal); mol (moles); mmol (millimoles); µmol (micromoles); nmol (nanomoles); g (grams); mg (milligrams); kg (kilograms); µg (micrograms); L (liters); ml (milliliters); µl (microliters); cm (centimeters); mm (millimeters); µm (micrometers); nm (nanometers); ° C. (degrees Centigrade); h (hours); min (minutes); sec (seconds); msec (milliseconds).

EXAMPLES

The present invention is described in further detain in the following examples which are not in any way intended to limit the scope of the invention as claimed. The attached Figures are meant to be considered as integral parts of the specification and description of the invention. All references cited are herein specifically incorporated by reference for all that is described therein. The following examples are offered to illustrate, but not to limit the claimed invention.

Example 1

Expression and Recovery

This example illustrates the expression and recovery of protein from bacterial host cells, e.g., E. coli.

DNA encoding the wild-type a-HL was purchased from a commercial source. The sequence was verified by sequencing.

Plasmid Construction.

The gene encoding either a wild-type or variant α-hemolysin was inserted into a pPR-IBA2 plasmid (IBA Life Sciences, Germany) under the control of T7 promoter.

Transformation.

E. coli BL21 DE3 (from Life Technologies) cells were transformed with the expression vector comprising the DNA encoding the wild-type or variant α-hemolysin using techniques well-known in the art. Briefly, the cells were thawed on ice (if frozen). Next, the desired DNA (in a suitable vector/plasmid) was added directly into the competent cells (should not exceed 5% of that of the competent cells) and mixed by flicking the tube. The tubes were placed on ice for 20 minutes. Next, the cells were placed in a 42° C. water bath for 45 seconds without mixing, followed by placing the tubes on ice for 2 min. The cells were then transferred to a 15 ml sterilized culture tube containing 0.9 ml of SOC medium (pre-warmed at room temperature) and cultured at 37° C. for 1 hr in a shaker. Finally, an aliquot of the cells were spread onto a LB agar plate containing the appropriate antibiotic and the plates incubated at 37° C. overnight.

Protein Expression.

Following transformation, colonies were picked and inoculated into a small volume (e.g., 3 ml) of growth medium (e.g., LB broth) containing the appropriate antibiotic with shaking at 37° C., overnight.

The next morning, transfer 1 ml of the overnight culture to a new 100 ml of autoinduction medium, e.g., Magic Media (Life Technologies) containing an appropriate antibiotic to select the expression plasmid. Grow the culture with shaking at 25° C. approximately 16 hrs but this depended on the expression plasmids. Cells were harvested by centrifugation at 3,000 g for 20 min at 4° C. and stored at −80° C. until used.

Purification.

Cells were lysed via sonication. The alpha-hemolysin was purified to homogeneity by affinity column chromatography.

Example 2

Alpha-Hemolysin Variants

The following example details the introduction of a mutation at a desired residue.

Mutations.

Site-directed mutagenesis is carried out using a QuikChange Multi Site-Directed Mutagenesis kit (Stratagene, La Jolla, Calif.) to prepare the example H35G+V149K+H144A, as set forth in SEQ ID NO: 4, but also including a C-terminal linker/TEV/HisTag for purification.

The variant was expressed and purified as in Example 1.

Example 3

Assembly of Nanopore Including Variant

This example describes the assembly of a nanopore comprising six a-HL variant subunits and one wild-type subunit.

The wild-type a-HL was expressed as described in Example 1 with SpyTag and a HisTag and purified on a cobalt affinity column using a cobalt elution buffer (200 mM NaCl, 300 mM imidazole, 50 mM tris, pH 8). The H35G+V149K+H144A a-HL variant was expressed as described in Example 1 with a HisTag and purified on a cobalt affinity column using a cobalt elution buffer (200 mM NaCl, 150 mM imidazole, 50 mM tris, pH 8). The protein was then incubated with 1 mg of TEV protease for every 5 mg of protein at 4° C. for 4 hours. After incubation with TEV protease the mixture is purified on a cobalt affinity column to remove TEV protease and undigested protein. The proteins were stored at 4° C. if used within 5 days, otherwise 8% trehalose was added and stored at −80° C.

Using approximately 10 mg of total protein, the α-HL/SpyTag to desired α-HL-variant protein solutions were mixed together at a 1:9 ratio to form a mixture of heptamers. It is expected that such a mixture will result in various fractions that include varying ratios of α-HL/SpyTag and α-HL-variant protein (0:7; 1:6, 2:5, 3:4, etc.), where the SpyTag component is present as 0, 1, 2, 3, 4, 5, 6, or seven monomeric subunits of the heptamer.

Diphytanoylphosphatidylcholine (DPhPC) lipid was solubilized in either 50 mM Tris, 200 mM NaCl, pH 8 or 150 mM KCl, 30 mM HEPES, pH 7.5 to a final concentration of 50 mg/ml and added to the mixture of a-HL monomers to a final concentration of 5 mg/ml. The mixture of the α-HL monomers was incubated at 37° C. for at least 60 min. Thereafter, n-Octyl-β-D-Glucopyranoside (βOG) was added to a final concentration of 5% (weight/volume) to solubilize the resulting lipid-protein mixture. The sample was centrifuged to clear protein aggregates and left over lipid complexes and the supernatant was collected for further purification.

The mixture of heptamers was then subjected to cation exchange purification and the elution fractions collected. For each fraction, two samples were prepared for SDS-PAGE. The first sample included 15 uL of α-HL eluate alone and the second sample was combined with 3 ug of SpyCatcher-GFP. The samples were then incubated and sheltered from light and at room temperature for 1-16 hours. Following incubation, 5 uL of 4× Laemmli SDS-PAGE buffer (Bio-Rad™) was added to each sample. The samples and a Precision-Plus™ Stain-Free protein ladder were then loaded onto a 4-20% Mini-PROTEAN Stain-Free protein precast gel (Bio-Rad). The gels were ran at 200 mV for 30 minutes. The gels were then imaged using a Stain-Free filter.

The conjugation of SpyCatcher-GFP to heptameric α-HL/SpyTag can be observed through molecular weight band shifts during SDS-PAGE. Heptamers containing a single SpyTag will bind a single SpyCatcher-GFP molecular and will thus have a shift that corresponds to the molecular weight of the heptameric pore plus the molecular weight of a single SpyCatcher-GFP, while heptamers with two or more SpyTags should have correspondingly larger molecular weight shifts. Therefore, the peaks eluted off of the cation exchange column during heptameric α-HL purification above can be analyzed for the ratio of α-HL/SpyTag to α-HL-variant. In addition, the presence of SpyCatcher-GFP attachment can be observed using a GFP-fluorescence filter when imaging the SDS-PAGE gels.

Based on this rationale, the fraction whose molecular weight shift corresponded to a single addition of Spy-Catcher-GFP was determined using a molecular weight standard protein ladder. Bio-Rad's stain-free imaging system was used to determine the molecular weight shift. The presence of GFP fluorescence was determined using a blue filter. The presence of fluorescence was used to confirm the presence of the SpyTag protein. The elution fraction corresponding to the 1:6 ratio, i.e., one α-HL/SpyTag to six α-HL-variants, was then used for further experiments.

Example 4

Attachment of a Polymerase

This example provides for the attachment of a polymerase to a nanopore.

The polymerase may be coupled to the nanopore by any suitable means. See, for example, PCT/US2013/068967 (published as WO2014/074727; Genia Technologies), PCT/US2005/009702 (published as WO2006/028508), and PCT/US2011/065640 (published as WO2012/083249; Columbia Univ).

The polymerase, e.g., phi29 DNA Polymerase, was coupled to a protein nanopore (e.g. alpha-hemolysin), through a linker molecule. Specifically, the SpyTag and SpyCatcher system, which spontaneously forms covalent isopeptide linkages under physiological conditions, was used. See, for example, Li et al, J Mol Biol. 2014 Jan. 23; 426(2):309-17.

Briefly, the Sticky phi29 SpyCatcher HisTag was expressed according to Example 1 and purified using a cobalt affinity column. The SpyCatcher polymerase and the SpyTag oligomerized protein were incubated at a 1:1 molar ratio overnight at 4° C. in 3 mM $SrCl_2$. The 1:6-polymerase-template complex is then purified using size-exclusion chromatography.

Example 5

Activity of the Variant

This example shows the activity of the nanopores as provided by Example 4 (nanopores with an attached polymerase).

The wild-type and H35G+V149K+H144A variant nanopores were assayed to determine the effect of the substitutions. More particularly, the assay was designed to measure the time it takes to capture a tagged molecule by a DNA polymerase attached to the nanopore using alternating voltages, i.e., squarewaves.

The bilayers were formed and pores were inserted as described in PCT/US14/61853 filed 23 Oct. 2014. The nanopore device (or sensor) used to detect a molecule (and/or sequence a nucleic acid) was set-up as described in WO2013123450.

To measure the time it takes to capture a tagged nucleotide by a DNA polymerase in our sequencing complex we have devised an assay that uses alternating positive and negative voltages (squarewaves) to determine the amount of time this takes. Our sequencing complex is comprised of a protein nanopore (αHL) which is attached to a single DNA polymerase (see Example 4). The tagged nucleotides are negatively charged, and are therefore attracted to the nanopore when the voltage applied is positive in nature, and repelled when the voltage applied to the nanopore sequencing complex is negative. So we can measure the time it takes for a tag to thread into the pore by cycling the voltage between positive and negative potentials and determine how much time the nanopore's current is unobstructed (open channel) verses when the tag is threaded (reduced current flux).

To carry out the "time-to-thread" assay, the Genia Sequencing device is used with a Genia Sequencing Chip. The electrodes are conditioned and phospholipid bilayers are established on the chip as explained in PCT/US2013/026514. Genia's sequencing complex is inserted to the bilayers following the protocol described in PCT/US2013/026514 (published as WO2013/123450). The time-to-thread data was collected using a buffer system comprised of 20 mM HEPES pH 8, 300 mM KGlu, 3 uM tagged nucleotide, 3 mM $Mg^{2+}$, with a voltage applied of 235 mV peak to peak with a duty cycle of 80 Hz.

After the data was collected, it was analyzed for squarewaves that showed the capture of a tagged nucleotide (threaded level) which lasted to the end of the positive portion of the squarewave, and was followed by another tag capture on the subsequent squarewave. The time-to-thread was measured by determining how long the second squarewave reported unobstructed open channel current. As an example, if 10 consecutive squarewaves showed tagged nucleotide captures that lasted to the end of the positive portion of the squarewave then the time-to-thread parameter would be calculated from squarewaves 2-10 (the first squarewave does not factor into the calculation because the polymerase did not have a tag bound to it in the previous squarewave). These time-to-thread numbers were then collected for all of the pores in the experiment and statistical parameters extracted from them (such as a mean, median, standard deviation etc.).

Figure 2:
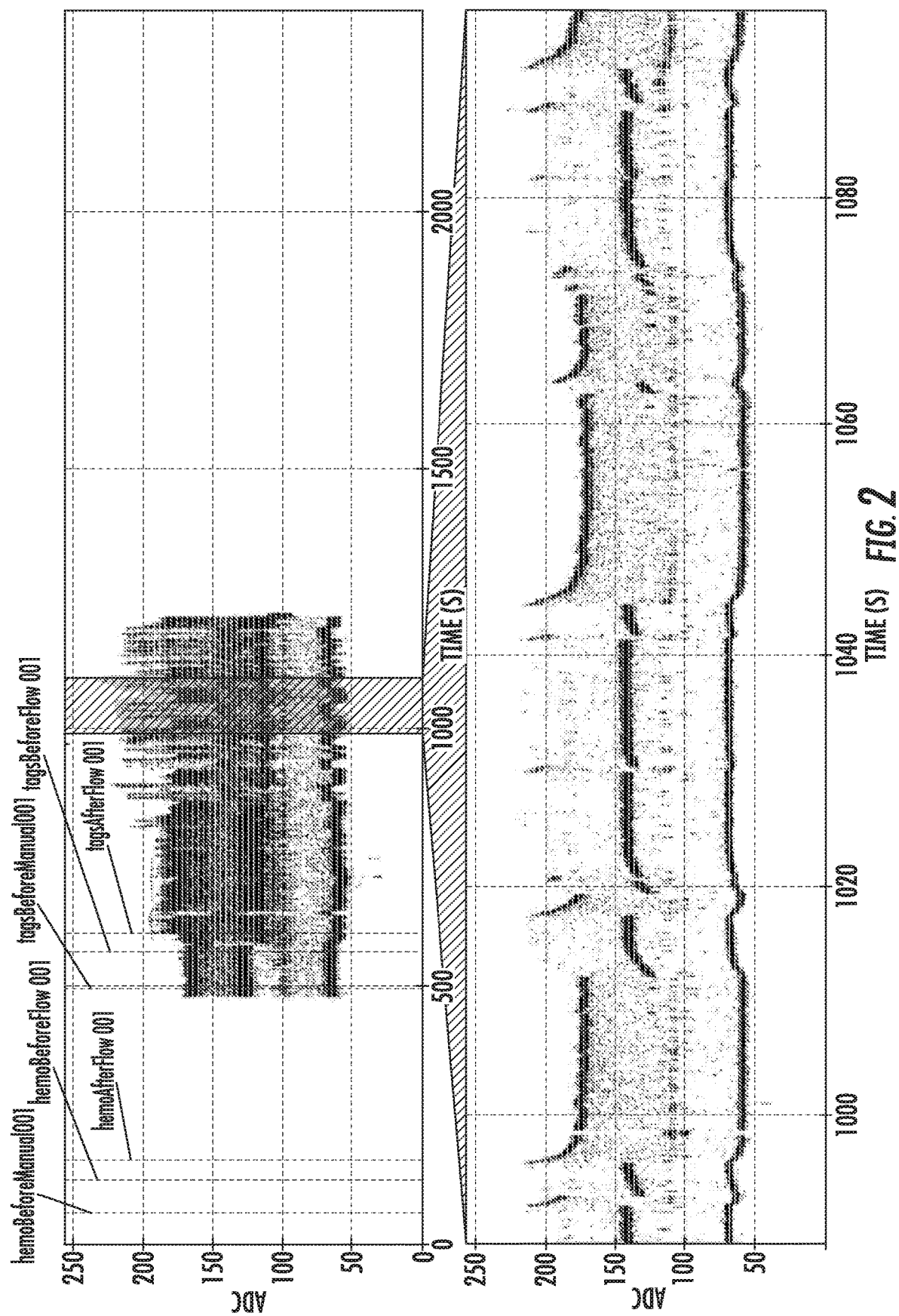
FIG. 2 is a graph showing the raw data used to generate FIG. 1.

Results for the H35G+V149K+H144A variant, as compared to controls, are shown in FIG. 1-2.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

| SEQUENCE LISTING FREE TEXT |
|---|
| SEQ ID NO: 1 (WT aHL DNA) |
| ATGGCAGATC TCGATCCCGC GAAATTAATA CGACTCACTA TAGGGAGGCC    50 |
| ACAACGGTTT CCCTCTAGAA ATAATTTTGT TTAACTTTAA GAAGGAGATA   100 |
| TACAAATGGA TTCAGATATT AATATTAAAA CAGGTACAAC AGATATTGGT   150 |
| TCAAATACAA CAGTAAAAAC TGGTGATTTA GTAACTTATG ATAAAGAAAA   200 |
| TGGTATGCAT AAAAAAGTAT TTTATTCTTT TATTGATGAT AAAAATCATA   250 |
| ATAAAAAATT GTTAGTTATT CGTACAAAAG GTACTATTGC AGGTCAATAT   300 |
| AGAGTATATA GTGAAGAAGG TGCTAATAAA AGTGGTTTAG CATGGCCATC   350 |
| TGCTTTTAAA GTTCAATTAC AATTACCTGA TAATGAAGTA GCACAAATTT   400 |
| CAGATTATTA TCCACGTAAT AGTATTGATA CAAAAGAATA TATGTCAACA   450 |
| TTAACTTATG GTTTTAATGG TAATGTAACA GGTGATGATA CTGGTAAAAT   500 |
| TGGTGGTTTA ATTGGTGCTA ATGTTTCAAT TGGTCATACA TTAAAATATG   550 |
| TACAACCAGA TTTTAAAACA ATTTTAGAAA GTCCTACTGA TAAAAAAGTT   600 |
| GGTTGGAAAG TAATTTTTAA TAATATGGTT AATCAAAATT GGGGTCCTTA   650 |
| TGATCGTGAT AGTTGGAATC CTGTATATGG TAATCAATTA TTTATGAAAA   700 |
| CAAGAAATGG TTCTATGAAA GCAGCTGATA ATTTCTTAGA TCCAAATAAA   750 |
| GCATCAAGTT TATTATCTTC AGGTTTTTCT CCTGATTTTG CAACAGTTAT   800 |
| TACTATGGAT AGAAAAGCAT CAAAACAACA AACAAATATT GATGTTATTT   850 |
| ATGAACGTGT AAGAGATGAT TATCAATTAC ATTGGACATC AACTAATTGG   900 |
| AAAGGTACAA ATACTAAAGA TAAATGGACA GATAGAAGTT CAGAAAGATA   950 |
| TAAAATTGAT TGGGAAAAAG AAGAAATGAC AAATGGTCTC AGCGCTTGGA  1000 |
| GCCACCCGCA GTTCGAAAAA TAA                                1023 |
| SEQ ID NO: 2 (WT aHL amino acids) [as expressed in E. coli] |
| MADSDINIKT GTTDIGSNTT VKTGDLVTYD KENGMHKKVF YSFIDDKNHN    50 |
| KKLLVIRTKG TIAGQYRVYS EEGANKSGLA WPSAFKVQLQ LPDNEVAQIS   100 |
| DYYPRNSIDT KEYMSTLTYG FNGNVTGDDT GKIGGLIGAN VSIGHTLKYV   150 |
| QPDFKTILES PTDKKVGWKV IFNNMVNQNW GPYDRDSWNP VYGNQLFMKT   200 |
| RNGSMKAADN FLDPNKASSL LSSGFSPDFA TVITMDRKAS KQQTNIDVIY   250 |
| ERVRDDYQLH WTSTNWKGTN TKDKWTDRSS ERYKIDWEKE EMTNGLSAWS   300 |
| HPQFEK                                                   306 |
| SEQ ID NO: 3 (Mature WT aHL, with purification tag) |
| ADSDINIKTG TTDIGSNTTV KTGDLVTYDK ENGMHKKVFY SFIDDKNHNK    50 |
| KLLVIRTKGT IAGQYRVYSE EGANKSGLAW PSAFKVQLQL PDNEVAQISD   100 |
| YYPRNSIDTK EYMSTLTYGF NGNVTGDDTG KIGGLIGANV SIGHTLKYVQ   150 |
| PDFKTILESP TDKKVGWKVI FNNMVNQNWG PYDRDSWNPV YGNQLFMKTR   200 |
| NGSMKAADNF LDPNKASSLL SSGFSPDFAT VITMDRKASK QQTNIDVIYE   250 |
| RVRDDYQLHW TSTNWKGTNT KDKWTDRSSE RYKIDWEKEE MTNGLSAWSH   300 |
| PQFEK                                                    305 |

SEQUENCE LISTING FREE TEXT

SEQ ID NO: 4 (H35G + V149K + H144A)
ADSDINIKTG TTDIGSNTTV KTGDLVTYDK ENGMGKKVFY SFIDDKNHNK 50

KLLVIRTKGT IAGQYRVYSE EGANKSGLAW PSAFKVQLQL PDNEVAQISD 100

YYPRNSIDTK EYMSTLTYGF NGNVTGDDTG KIGGLIGANV SIGATLKYKQ 150

PDFKTILESP TDKKVGWKVI FNNMVNQNWG PYDRDSWNPV YGNQLFMKTR 200

NGSMKAADNF LDPNKASSLL SSGFSPDFAT VITMDRKASK QQTNIDVIYE 250

RVRDDYQLHW TSTNWKGTNT KDKWTDRSSE RYKIDWEKEE MTN 293

SEQ ID NO: 5 (H35G + H144A + V149K + E287R)
ADSDINIKTG TTDIGSNTTV KTGDLVTYDK ENGMGKKVFY SFIDDKNHNK 50

KLLVIRTKGT IAGQYRVYSE EGANKSGLAW PSAFKVQLQL PDNEVAQISD 100

YYPRNSIDTK EYMSTLTYGF NGNVTGDDTG KIGGLIGANV SIGATLKYKQ 150

PDFKTILESP TDKKVGWKVI FNNMVNQNWG PYDRDSWNPV YGNQLFMKTR 200

NGSMKAADNF LDPNKASSLL SSGFSPDFAT VITMDRKASK QQTNIDVIYE 250

RVRDDYQLHW TSTNWKGTNT KDKWTDRSSE RYKIDWRKEE MTN 293

SEQ ID NO: 6 (V149K + E287R)
ADSDINIKTG TTDIGSNTTV KTGDLVTYDK ENGMGKKVFY SFIDDKNHNK 50

KLLVIRTKGT IAGQYRVYSE EGANKSGLAW PSAFKVQLQL PDNEVAQISD 100

YYPRNSIDTK EYMSTLTYGF NGNVTGDDTG KIGGLIGANV SIGHTLKYKQ 150

PDFKTILESP TDKKVGWKVI FNNMVNQNWG PYDRDSWNPV YGNQLFMKTR 200

NGSMKAADNF LDPNKASSLL SSGFSPDFAT VITMDRKASK QQTNIDVIYE 250

RVRDDYQLHW TSTNWKGTNT KDKWTDRSSE RYKIDWRKEE MTN 293

SEQ ID NO: 7 (T109K + H35G)
ADSDINIKTG TTDIGSNTTV KTGDLVTYDK ENGMGKKVFY SFIDDKNHNK 50

KLLVIRTKGT IAGQYRVYSE EGANKSGLAW PSAFKVQLQL PDNEVAQISD 100

YYPRNSIDKK EYMSTLTYGF NGNVTGDDTG KIGGLIGANV SIGATLKYVQ 150

PDFKTILESP TDKKVGWKVI FNNMVNQNWG PYDRDSWNPV YGNQLFMKTR 200

NGSMKAADNF LDPNKASSLL SSGFSPDFAT VITMDRKASK QQTNIDVIYE 250

RVRDDYQLHW TSTNWKGTNT KDKWTDRSSE RYKIDWEKEE MTN 293

SEQ ID NO: 8 (P151K + H35G)
ADSDINIKTG TTDIGSNTTV KTGDLVTYDK ENGMGKKVFY SFIDDKNHNK 50

KLLVIRTKGT IAGQYRVYSE EGANKSGLAW PSAFKVQLQL PDNEVAQISD 100

YYPRNSIDTK EYMSTLTYGF NGNVTGDDTG KIGGLIGANV SIGATLKYVQ 150

KDFKTILESP TDKKVGWKVI FNNMVNQNWG PYDRDSWNPV YGNQLFMKTR 200

NGSMKAADNF LDPNKASSLL SSGFSPDFAT VITMDRKASK QQTNIDVIYE 250

RVRDDYQLHW TSTNWKGTNT KDKWTDRSSE RYKIDWEKEE MTN 293

SEQ ID NO: 9 (V149K + P151K + H35G)
ADSDINIKTG TTDIGSNTTV KTGDLVTYDK ENGMGKKVFY SFIDDKNHNK 50

KLLVIRTKGT IAGQYRVYSE EGANKSGLAW PSAFKVQLQL PDNEVAQISD 100

YYPRNSIDTK EYMSTLTYGF NGNVTGDDTG KIGGLIGANV SIGATLKYKQ 150

KDFKTILESP TDKKVGWKVI FNNMVNQNWG PYDRDSWNPV YGNQLFMKTR 200

SEQUENCE LISTING FREE TEXT

```
NGSMKAADNF LDPNKASSLL SSGFSPDFAT VITMDRKASK QQTNIDVIYE  250

RVRDDYQLHW TSTNWKGTNT KDKWTDRSSE RYKIDWEKEE MTN         293

SEQ ID NO: 10 (T109K + V149K + H35G)
ADSDINIKTG TTDIGSNTTV KTGDLVTYDK ENGMGKKVFY SFIDDKNHNK   50

KLLVIRTKGT IAGQYRVYSE EGANKSGLAW PSAFKVQLQL PDNEVAQISD  100

YYPRNSIDKK EYMSTLTYGF NGNVTGDDTG KIGGLIGANV SIGATLKYKQ  150

PDFKTILESP TDKKVGWKVI FNNMVNQNWG PYDRDSWNPV YGNQLFMKTR  200

NGSMKAADNF LDPNKASSLL SSGFSPDFAT VITMDRKASK QQTNIDVIYE  250

RVRDDYQLHW TSTNWKGTNT KDKWTDRSSE RYKIDWEKEE MTN         293

SEQ ID NO: 11 (V149K + K147N + E111N + 127-131G + M113A +
H35G)
ADSDINIKTG TTDIGSNTTV KTGDLVTYDK ENGMGKKVFY SFIDDKNHNK   50

KLLVIRTKGT IAGQYRVYSE EGANKSGLAW PSAFKVQLQL PDNEVAQISD  100

YYPRNSIDTK NYASTLTYGF NGNVTGGGGG GIGGLIGANV SIGATLNYKQ  150

PDFKTILESP TDKKVGWKVI FNNMVNQNWG PYDRDSWNPV YGNQLFMKTR  200

NGSMKAADNF LDPNKASSLL SSGFSPDFAT VITMDRKASK QQTNIDVIYE  250

RVRDDYQLHW TSTNWKGTNT KDKWTDRSSE RYKIDWEKEE MTN         293

SEQ ID NO: 12 (V149K + K147N + E111N + 127-131G + M113A)
ADSDINIKTG TTDIGSNTTV KTGDLVTYDK ENGMHKKVFY SFIDDKNHNK   50

KLLVIRTKGT IAGQYRVYSE EGANKSGLAW PSAFKVQLQL PDNEVAQISD  100

YYPRNSIDTK NYASTLTYGF NGNVTGGGGG GIGGLIGANV SIGHTLNYKQ  150

PDFKTILESP TDKKVGWKVI FNNMVNQNWG PYDRDSWNPV YGNQLFMKTR  200

NGSMKAADNF LDPNKASSLL SSGFSPDFAT VITMDRKASK QQTNIDVIYE  250

RVRDDYQLHW TSTNWKGTNT KDKWTDRSSE RYKIDWEKEE MTN         293

SEQ ID NO: 13 (T109K + V149K + P151K + H35G)
ADSDINIKTG TTDIGSNTTV KTGDLVTYDK ENGMGKKVFY SFIDDKNHNK   50

KLLVIRTKGT IAGQYRVYSE EGANKSGLAW PSAFKVQLQL PDNEVAQISD  100

YYPRNSIDKK EYMSTLTYGF NGNVTGDDTG KIGGLIGANV SIGATLKYKQ  150

KDFKTILESP TDKKVGWKVI FNNMVNQNWG PYDRDSWNPV YGNQLFMKTR  200

NGSMKAADNF LDPNKASSLL SSGFSPDFAT VITMDRKASK QQTNIDVIYE  250

RVRDDYQLHW TSTNWKGTNT KDKWTDRSSE RYKIDWEKEE MIN         293

SEQ ID NO: 14 (Mature WT aHL; AAA26598)
ADSDINIKTG TTDIGSNTTV KTGDLVTYDK ENGMHKKVFY SFIDDKNHNK   50

KLLVIRTKGT IAGQYRVYSE EGANKSGLAW PSAFKVQLQL PDNEVAQISD  100

YYPRNSIDTK EYMSTLTYGF NGNVTGDDTG KIGGLIGANV SIGHTLKYVQ  150

PDFKTILESP TDKKVGWKVI FNNMVNQNWG PYDRDSWNPV YGNQLFMKTR  200

NGSMKAADNF LDPNKASSLL SSGFSPDFAT VITMDRKASK QQTNIDVIYE  250

RVRDDYQLHW TSTNWKGTNT KDKWTDRSSE RYKIDWEKEE MTN         293

SEQ ID NO: 15 (13016 with His Taq)
MHHHHHHHHS GGSDKHTQYV KEHSFNYDEY KKANFDKIEC LIFDTESCTN   50

YENDNTGARV YGWGLGVTRN HNMIYGQNLN QFWEVCQNIF NDWYHDNKHT  100

IKITKTKKGF PKRKYIKFPI AVHNLGWDVE FLKYSLVENG FNYDKGLLKT  150
```

| SEQUENCE LISTING FREE TEXT |
|---|
| VFSKGAPYQT VTDVEEPKTF HIVQNNNIVY GCNVYMDKFF EVENKDGSTT 200 |
| EIGLCLDFFD SYKIITCAES QFHNYVHDVD PMFYKMGEEY DYDTWRSPTH 250 |
| KQTTLELRYQ YNDIYMLREV IEQFYIDGLC GGELPLTGMR TASSIAFNVL 300 |
| KKMTFGEEKT EEGYINYFEL DKKTKFEFLR KRIEMESYTG GYTHANHKAV 350 |
| GKTINKIGCS LDINSSYPSQ MAYKVFPYGK PVRKTWGRKP KTEKNEVYLI 400 |
| EVGFDFVEPK HEEYALDIFK IGAVNSKALS PITGAVSGQE YFCTNIKDGK 450 |
| AIPVYKELKD TKLTTNYNVV LTSVEYEFWI KHFNFGVFKK DEYDCFEVDN 500 |
| LEFTGLKIGS ILYYKAEKGK FKPYVDHFTK MKVENKKLGN KPLTNQAKLI 550 |
| LNGAYGKFGT KQNKEEKDLI MDKNGLLTFT GSVTEYEGKE FYRPYASFVT 600 |
| AYGRLQLWNA IIYAVGVENF LYCDTDSIYC NREVNSLIED MNAIGETIDK 650 |
| TILGKWDVEH VFDKFKVLGQ KKYMYHDCKE DKTDLKCCGL PSDARKIIIG 700 |
| QGFDEFYLGK NVEGKKQRKK VIGGCLLLDT LFTIKKIMF* 739 |
| SEQ ID NO: 16 (Linker/TEV/HisTaq (TEV portion underlined) GLSA<u>ENLYFQG</u>HHHHHH |

CITATION LIST

Patent Literature

[1] PCT/US2013/026514 (published as WO2013/123450) entitled "Methods for Creating Bilayers for Use with Nanopore Sensors"
[2] PCT/US2013/068967 (published as WO 2014/074727) entitled "Nucleic Acid Sequencing Using Tags"
[3] PCT/US14/61853 filed 23 Oct. 2014 entitled "Methods for Forming Lipid Bilayers on Biochips"

Non-Patent Literature

[4] Aksimentiev and Schulten, *Imaging a-Hemolysin with Molecular Dynamics: Ionic Conductance, Osmotic Permeability, and the Electrostatic Potential Map*, Biophysical Journal (2005) 88: 3745-3761.
[5] Butler et al., *Single-molecule DNA detection with an engineered MspA protein nanopore*, PNAS (2008) 105 (52): 20647-20652.
[6] Korchev et al., *Low Conductance States of a Single Ion Channel are not 'Closed'*, J. Membrane Biol. (1995) 147:233-239.
[7] Krasilnikov and Sabirov, *Ion Transport Through Channels Formed in Lipid Bilayers by Staphylococcus aureus Alpha-Toxin*, Gen. Physiol. Biophys. (1989) 8:213-222.
[8] Nakane et al., *A Nanosensor for Transmembrane Capture and Identification of Single Nucleic Acid Molecules*, Biophys. J. (2004) 87:615-621.
[9] Rhee and Burns, *Nanopore sequencing technology: nanopore preparations*, TRENDS in Biotech. (2007) 25(4):174-181.
[10] Song et al., *Structure of Staphylococcal α-Hemolysin, a Heptameric Transmembrane Pore*, Science (1996) 274: 1859-1866.
[11] Kasianowicz et al., *Nanometer-scale pores: potential applications for analyte detection and DNA characterization*, Proc. Natl. Acad. Sci. USA (1996) 93:13770-13773.
[12] Akeson et al., *Microsecond timescale discrimination among polycytidylic acid, polyadenylic acid, and polyuridylic acid as homopolymers or as segments within single RNA molecules*, Biophys. J. (1999) 77:3227-3233.
[13] Meller et al., *Voltage-driven DNA translocations through a nanopore*, Phys. Rev. Lett., 86 (2001), pp. 3435-3438.
[14] Howorka et al., *Sequence-specific detection of individual DNA strands using engineered nanopores*, Nat. Biotechnol., 19 (2001a), pp. 636-639.
[15] Howorka et al., *Kinetics of duplex formation for individual DNA strands within a single protein nanopore*, Proc. Natl. Acad. Sci. USA, 98 (2001b), pp. 12996-13001.
[16] Movileanu et al., *Detecting protein analytes that modulate transmembrane movement of a polymer chain within a single protein pore*, Nat. Biotechnol., 18 (2000), pp. 1091-1095.

The entirety of each patent, patent application, publication, document, GENBANK sequence, website and other published material referenced herein hereby is incorporated by reference, including all tables, drawings, and figures. All patents and publications are herein incorporated by reference to the same extent as if each was specifically and individually indicated to be incorporated by reference. Citation of the above patents, patent applications, publications and documents is not an admission that any of the foregoing is pertinent prior art, nor does it constitute any admission as to the contents or date of these publications or documents. All patents and publications mentioned herein are indicative of the skill levels of those of ordinary skill in the art to which the invention pertains.

What is claimed is:

1. An α-hemolysin variant having at least 90% sequence identity to one or more of SEQ ID NOs: 5-14, wherein said amino acid sequence has a set of substitutions relative to SEQ ID NO: 14 comprising at least one of the following substitution combinations:

(a) H35G+V149K;

(b) H35G+V149K+E287R;

(c) V149K+E287R;

(d) H35G+T109K;

(e) H35G+P151K;

(f) H35G+V149K+P151K;

(g) H35G+T109K+V149K;

(h) H35G+E111N+M113A+D127G+D128G+T129G+K131G+K147N+V149K;

(i) E111N+M113A+D127G+D128+T129G+K131G+K147N+V149K;

(j) H353G+T109K+V149K+P151K; and (k) H35G+H144A+V149K+E287R.

2. The α-hemolysin variant of claim 1, wherein said set of substitutions further comprise substitutions corresponding to positions of SEQ 10 NO: 14 selected from the group consisting of 1-6, 8-11, 13-22, 24-33, 35-37, 40, 44-51, 56, 62, 64-75, 79, 82, 83, 85, 87, 89-95, 97, 102-118, 120-132, 134-156, 158-164, 168, 170-191, 193, 194, 197-205, 207, 208, 210-216, 218, 221, 222, 224-229, 235-241, 244, 246, 250, 252, 253, 255, 257, 259-264, 266, 268-278, 280-283, 285-289, and 291-293.

3. The α-hemolysin variant of claim 1, wherein said set of substitutions (a) through (j) further comprises an H144A substitution.

4. The α-hemolysin variant of claim 1, wherein said set of substitutions further comprises an alanine, asparagine, or lysine substitution at one or more of residues 1-17 of SEQ ID NO: 14.

5. The α-hemolysin variant of claim 1, wherein said set of substitutions (a) through (g), (j), and (k) further comprises a series of glycine residues at positions corresponding to each of residues 127-131 of SEQ ID NO: 14.

6. The α-hemolysin variant of claim 1, wherein the amino acid sequence comprises SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13.

7. The α-hemolysin variant of claim 1, wherein the amino acid sequence consists of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13.

8. The α-hemolysin variant of claim 1, further comprising a purification tag.

9. The α-hemolysin variant of claim 1, further comprising a polymerase attached thereto.

10. The α-hemolysin variant of claim 9, wherein the polymerase is a DNA polymerase.

11. The α-hemolysin variant of claim 10, wherein the DNA polymerase is covalently attached to the isolated polypeptide.

12. A heptameric nanopore assembly comprising 7 alpha-hemolysin subunits arranged in a nanopore, wherein at least one of the seven alpha-hemolysin subunits comprises the isolated α-hemolysin variant of claim 1 and a DNA polymerase covalently attached to one of the seven alpha-hemolysin subunits.

13. The heptameric nanopore assembly of claim 12, wherein the nanopore is a heteromeric pore.

14. The heptameric nanopore assembly of claim 12, wherein the nanopore is a homomeric pore.

15. The heptameric nanopore assembly of claim 12, wherein the nanopore has a decreased time to thread (TTT) relative to a heptameric nanopore assembly consisting of native alpha-hemolysins.

16. The heptameric nanopore assembly of claim 15, wherein the nanopore has at least a 10% decreased TTT relative to the heptameric nanopore assembly consisting of native alpha-hemolysins.

17. The heptameric nanopore assembly of claim 15, wherein the nanopore has at least a 50% decreased TTT relative to the heptameric nanopore assembly consisting of native alpha-hemolysins.

18. The heptameric nanopore assembly of claim 15, wherein the nanopore has at least an 80% decreased TTT relative to the heptameric nanopore assembly consisting of native alpha-hemolysins.

19. A system for sequencing a nucleic acid comprising: a heptameric nanopore assembly according to claim 12; a chip comprising a plurality of sensing electrodes and a membrane that is disposed adjacent or in proximity to one or more of the sensing electrodes; and a set of negatively charged tagged nucleotides.

20. A method for sequencing a target nucleic acid sequence, comprising: providing a chip, the chip comprising a plurality of sensing electrodes and a membrane that is disposed adjacent or in proximity to the sensing electrodes; disposing, within the membrane, a heptameric nanopore assembly of claim 12; contacting the chip with a target nucleic acid sequence and a plurality of negatively charged tagged nucleotides; applying a voltage across the membrane; determining, by one or more of the sensing electrodes, one or more current changes associated with the heptameric nanopore assembly; and determining, with the aid of a computer processor and based on the one or more of the determined current changes associated with the heptameric nanopore assembly, a sequence for the target nucleic acid sequence.

21. The method of claim 20, wherein the chip comprises a well and wherein the nanopore assembly is disposed within the membrane over the well.

22. The method of claim 20, wherein the nucleic acid comprises a tag.

23. The method of claim 22, wherein the tag is a negatively charged tag.

* * * * *

UNITED STATES PATENT AND TRADEMARK OFFICE
CERTIFICATE OF CORRECTION

| | |
|---|---|
| PATENT NO. | : 10,968,480 B2 |
| APPLICATION NO. | : 16/425743 |
| DATED | : April 6, 2021 |
| INVENTOR(S) | : Timothy K. Craig et al. |

It is certified that error appears in the above-identified patent and that said Letters Patent is hereby corrected as shown below:

In the Claims

Claim 1, Column 58, Line 66, should be corrected to read "H35G+T109K+V149K+P151K; and"

Signed and Sealed this
Fourteenth Day of March, 2023

Katherine Kelly Vidal
*Director of the United States Patent and Trademark Office*

SEQUENCE LISTING

<160> NUMBER OF SEQ ID NOS: 16

<210> SEQ ID NO 1
<211> LENGTH: 1023
<212> TYPE: DNA
<213> ORGANISM: Staphylococcus aureus

<400> SEQUENCE: 1

```
atggcagatc tcgatcccgc gaaattaata cgactcacta tagggaggcc acaacggttt      60
ccctctagaa ataattttgt ttaactttaa gaaggagata tacaaatgga ttcagatatt     120
aatattaaaa caggtacaac agatattggt tcaaatacaa cagtaaaaac tggtgattta     180
gtaacttatg ataagaaaaa tggtatgcat aaaaaagtat tttattcttt tattgatgat     240
aaaaatcata taaaaaatt gttagttatt cgtacaaaag gtactattgc aggtcaatat     300
agagtatata gtgaagaagg tgctaataaa agtggtttag catggccatc tgcttttaaa     360
gttcaattac aattacctga taatgaagta gcacaaattt cagattatta tccacgtaat     420
agtattgata caaagaata tatgtcaaca ttaacttatg gttttaatgg taatgtaaca     480
ggtgatgata ctggtaaaat tggtggttta attggtgcta atgtttcaat tggtcataca     540
ttaaaatatg tacaaccaga tttaaaaca attttagaaa gtcctactga taaaaaagtt     600
ggttggaaag taattttaa taatatggtt aatcaaaatt ggggtcctta tgatcgtgat     660
agttggaatc ctgtatatgg taatcaatta tttatgaaaa caagaaatgg ttctatgaaa     720
gcagctgata atttcttaga tccaaataaa gcatcaagtt tattatcttc aggttttct     780
cctgattttg caacagttat tactatggat agaaaagcat caaaacaaca aacaaatatt     840
gatgttattt atgaacgtgt aagagatgat tatcaattac attggacatc aactaattgg     900
aaaggtacaa atactaaaga taatggaca gatagaagtt cagaaagata taaaattgat     960
tgggaaaaag aagaaatgac aaatggtctc agcgcttgga gccacccgca gttcgaaaaa    1020
taa                                                                  1023
```

<210> SEQ ID NO 2
<211> LENGTH: 306
<212> TYPE: PRT
<213> ORGANISM: Staphylococcus aureus

<400> SEQUENCE: 2

Met Ala Asp Ser Asp Ile Asn Ile Lys Thr Gly Thr Thr Asp Ile Gly
1               5                   10                  15

Ser Asn Thr Thr Val Lys Thr Gly Asp Leu Val Thr Tyr Asp Lys Glu
            20                  25                  30

Asn Gly Met His Lys Lys Val Phe Tyr Ser Phe Ile Asp Asp Lys Asn
        35                  40                  45

His Asn Lys Lys Leu Leu Val Ile Arg Thr Lys Gly Thr Ile Ala Gly
    50                  55                  60

Gln Tyr Arg Val Tyr Ser Glu Glu Gly Ala Asn Lys Ser Gly Leu Ala
65                  70                  75                  80

Trp Pro Ser Ala Phe Lys Val Gln Leu Gln Leu Pro Asp Asn Glu Val
                85                  90                  95

Ala Gln Ile Ser Asp Tyr Tyr Pro Arg Asn Ser Ile Asp Thr Lys Glu
            100                 105                 110

Tyr Met Ser Thr Leu Thr Tyr Gly Phe Asn Gly Asn Val Thr Gly Asp
        115                 120                 125

Asp Thr Gly Lys Ile Gly Gly Leu Ile Gly Ala Asn Val Ser Ile Gly

```
            130                 135                 140
His Thr Leu Lys Tyr Val Gln Pro Asp Phe Lys Thr Ile Leu Glu Ser
145                 150                 155                 160

Pro Thr Asp Lys Lys Val Gly Trp Lys Val Ile Phe Asn Asn Met Val
                165                 170                 175

Asn Gln Asn Trp Gly Pro Tyr Asp Arg Asp Ser Trp Asn Pro Val Tyr
            180                 185                 190

Gly Asn Gln Leu Phe Met Lys Thr Arg Asn Gly Ser Met Lys Ala Ala
                195                 200                 205

Asp Asn Phe Leu Asp Pro Asn Lys Ala Ser Ser Leu Leu Ser Ser Gly
            210                 215                 220

Phe Ser Pro Asp Phe Ala Thr Val Ile Thr Met Asp Arg Lys Ala Ser
225                 230                 235                 240

Lys Gln Gln Thr Asn Ile Asp Val Ile Tyr Glu Arg Val Arg Asp Asp
                245                 250                 255

Tyr Gln Leu His Trp Thr Ser Thr Asn Trp Lys Gly Thr Asn Thr Lys
            260                 265                 270

Asp Lys Trp Thr Asp Arg Ser Ser Glu Arg Tyr Lys Ile Asp Trp Glu
                275                 280                 285

Lys Glu Glu Met Thr Asn Gly Leu Ser Ala Trp Ser His Pro Gln Phe
            290                 295                 300

Glu Lys
305

<210> SEQ ID NO 3
<211> LENGTH: 305
<212> TYPE: PRT
<213> ORGANISM: Staphylococcus aureus

<400> SEQUENCE: 3

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
65              70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190
```

```
Asn Gln Leu Phe Met Lys Thr Arg Asn Gly Ser Met Lys Ala Ala Asp
            195                 200                 205

Asn Phe Leu Asp Pro Asn Lys Ala Ser Ser Leu Leu Ser Ser Gly Phe
        210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn Gly Leu Ser Ala Trp Ser His Pro Gln Phe Glu
    290                 295                 300

Lys
305

<210> SEQ ID NO 4
<211> LENGTH: 293
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met Gly Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly Ala
    130                 135                 140

Thr Leu Lys Tyr Lys Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240
```

```
Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290

<210> SEQ ID NO 5
<211> LENGTH: 293
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met Gly Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly Ala
130                 135                 140

Thr Leu Lys Tyr Lys Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Arg Lys
        275                 280                 285

Glu Glu Met Thr Asn
```

<210> SEQ ID NO 6
<211> LENGTH: 293
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met Gly Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Lys Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Arg Lys
    275                 280                 285

Glu Glu Met Thr Asn
    290
```

<210> SEQ ID NO 7
<211> LENGTH: 293
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 7

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met Gly Lys Lys Val Phe Tyr Ser Phe Ile Asp Asp Lys Asn His
        35                  40                  45

Asn Lys Lys Leu Leu Val Ile Arg Thr Lys Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Lys Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly Ala
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290
```

<210> SEQ ID NO 8
<211> LENGTH: 293
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met Gly Lys Lys Val Phe Tyr Ser Phe Ile Asp Asp Lys Asn His
        35                  40                  45
```

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly Ala
130                 135                 140

Thr Leu Lys Tyr Val Gln Lys Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
        290

<210> SEQ ID NO 9
<211> LENGTH: 293
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met Gly Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

```
Met Ser Thr Leu Thr Tyr Gly Phe Asn Gly Asn Val Thr Gly Asp Asp
            115                 120                 125

Thr Gly Lys Ile Gly Gly Leu Ile Gly Ala Asn Val Ser Ile Gly Ala
        130                 135                 140

Thr Leu Lys Tyr Lys Gln Lys Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
        290

<210> SEQ ID NO 10
<211> LENGTH: 293
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met Gly Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Lys Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly Ala
    130                 135                 140

Thr Leu Lys Tyr Lys Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
```

```
            165                 170                 175
Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
            195                 200                 205

Asn Phe Leu Asp Pro Asn Lys Ala Ser Ser Leu Leu Ser Ser Gly Phe
            210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
            245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
            275                 280                 285

Glu Glu Met Thr Asn
            290

<210> SEQ ID NO 11
<211> LENGTH: 293
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met Gly Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
            85                  90                  95

Gln Ile Ser Asp Tyr Tyr Pro Arg Asn Ser Ile Asp Thr Lys Asn Tyr
            100                 105                 110

Ala Ser Thr Leu Thr Tyr Gly Phe Asn Gly Asn Val Thr Gly Gly Gly
            115                 120                 125

Gly Gly Gly Ile Gly Gly Leu Ile Gly Ala Asn Val Ser Ile Gly Ala
        130                 135                 140

Thr Leu Asn Tyr Lys Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
            165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
            195                 200                 205

Asn Phe Leu Asp Pro Asn Lys Ala Ser Ser Leu Leu Ser Ser Gly Phe
            210                 215                 220
```

```
Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
            245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290

<210> SEQ ID NO 12
<211> LENGTH: 293
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Asn Tyr
            100                 105                 110

Ala Ser Thr Leu Thr Tyr Gly Phe Asn Gly Asn Val Thr Gly Gly Gly
        115                 120                 125

Gly Gly Gly Ile Gly Gly Leu Ile Gly Ala Asn Val Ser Ile Gly His
    130                 135                 140

Thr Leu Asn Tyr Lys Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285
```

Glu Glu Met Thr Asn
       290

<210> SEQ ID NO 13
<211> LENGTH: 293
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met Gly Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Lys Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly Ala
    130                 135                 140

Thr Leu Lys Tyr Lys Gln Lys Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290

<210> SEQ ID NO 14
<211> LENGTH: 293
<212> TYPE: PRT
<213> ORGANISM: Staphylococcus aureus

<400> SEQUENCE: 14

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290

<210> SEQ ID NO 15
<211> LENGTH: 739
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met His His His His His His Ser Gly Gly Ser Asp Lys His
1               5                   10                  15

Thr Gln Tyr Val Lys Glu His Ser Phe Asn Tyr Asp Glu Tyr Lys Lys
            20                  25                  30

Ala Asn Phe Asp Lys Ile Glu Cys Leu Ile Phe Asp Thr Glu Ser Cys
        35                  40                  45

Thr Asn Tyr Glu Asn Asp Asn Thr Gly Ala Arg Val Tyr Gly Trp Gly

```
                50                  55                  60
Leu Gly Val Thr Arg Asn His Asn Met Ile Tyr Gly Gln Asn Leu Asn
 65                  70                  75                  80

Gln Phe Trp Glu Val Cys Gln Asn Ile Phe Asn Asp Trp Tyr His Asp
                 85                  90                  95

Asn Lys His Thr Ile Lys Ile Thr Lys Thr Lys Gly Phe Pro Lys
                100                 105                 110

Arg Lys Tyr Ile Lys Phe Pro Ile Ala Val His Asn Leu Gly Trp Asp
                115                 120                 125

Val Glu Phe Leu Lys Tyr Ser Leu Val Glu Asn Gly Phe Asn Tyr Asp
                130                 135                 140

Lys Gly Leu Leu Lys Thr Val Phe Ser Lys Gly Ala Pro Tyr Gln Thr
145                 150                 155                 160

Val Thr Asp Val Glu Glu Pro Lys Thr Phe His Ile Val Gln Asn Asn
                165                 170                 175

Asn Ile Val Tyr Gly Cys Asn Val Tyr Met Asp Lys Phe Phe Glu Val
                180                 185                 190

Glu Asn Lys Asp Gly Ser Thr Thr Glu Ile Gly Leu Cys Leu Asp Phe
                195                 200                 205

Phe Asp Ser Tyr Lys Ile Ile Thr Cys Ala Glu Ser Gln Phe His Asn
                210                 215                 220

Tyr Val His Asp Val Asp Pro Met Phe Tyr Lys Met Gly Glu Glu Tyr
225                 230                 235                 240

Asp Tyr Asp Thr Trp Arg Ser Pro Thr His Lys Gln Thr Thr Leu Glu
                245                 250                 255

Leu Arg Tyr Gln Tyr Asn Asp Ile Tyr Met Leu Arg Glu Val Ile Glu
                260                 265                 270

Gln Phe Tyr Ile Asp Gly Leu Cys Gly Gly Glu Leu Pro Leu Thr Gly
                275                 280                 285

Met Arg Thr Ala Ser Ser Ile Ala Phe Asn Val Leu Lys Lys Met Thr
                290                 295                 300

Phe Gly Glu Glu Lys Thr Glu Glu Gly Tyr Ile Asn Tyr Phe Glu Leu
305                 310                 315                 320

Asp Lys Lys Thr Lys Phe Glu Phe Leu Arg Lys Arg Ile Glu Met Glu
                325                 330                 335

Ser Tyr Thr Gly Gly Tyr Thr His Ala Asn His Lys Ala Val Gly Lys
                340                 345                 350

Thr Ile Asn Lys Ile Gly Cys Ser Leu Asp Ile Asn Ser Ser Tyr Pro
                355                 360                 365

Ser Gln Met Ala Tyr Lys Val Phe Pro Tyr Gly Lys Pro Val Arg Lys
                370                 375                 380

Thr Trp Gly Arg Lys Pro Lys Thr Glu Lys Asn Glu Val Tyr Leu Ile
385                 390                 395                 400

Glu Val Gly Phe Asp Phe Val Glu Pro Lys His Glu Glu Tyr Ala Leu
                405                 410                 415

Asp Ile Phe Lys Ile Gly Ala Val Asn Ser Lys Ala Leu Ser Pro Ile
                420                 425                 430

Thr Gly Ala Val Ser Gly Gln Glu Tyr Phe Cys Thr Asn Ile Lys Asp
                435                 440                 445

Gly Lys Ala Ile Pro Val Tyr Lys Glu Leu Lys Asp Thr Lys Leu Thr
                450                 455                 460

Thr Asn Tyr Asn Val Val Leu Ser Val Glu Tyr Glu Phe Trp Ile
465                 470                 475                 480
```

```
Lys His Phe Asn Phe Gly Val Phe Lys Lys Asp Glu Tyr Asp Cys Phe
                485             490                 495
Glu Val Asp Asn Leu Glu Phe Thr Gly Leu Lys Ile Gly Ser Ile Leu
            500             505                 510
Tyr Tyr Lys Ala Glu Lys Gly Lys Phe Lys Pro Tyr Val Asp His Phe
        515             520                 525
Thr Lys Met Lys Val Glu Asn Lys Lys Leu Gly Asn Lys Pro Leu Thr
        530             535             540
Asn Gln Ala Lys Leu Ile Leu Asn Gly Ala Tyr Gly Lys Phe Gly Thr
545             550              555                 560
Lys Gln Asn Lys Glu Glu Lys Asp Leu Ile Met Asp Lys Asn Gly Leu
                565             570                 575
Leu Thr Phe Thr Gly Ser Val Thr Glu Tyr Glu Gly Lys Glu Phe Tyr
            580             585                 590
Arg Pro Tyr Ala Ser Phe Val Thr Ala Tyr Gly Arg Leu Gln Leu Trp
        595             600             605
Asn Ala Ile Ile Tyr Ala Val Gly Val Glu Asn Phe Leu Tyr Cys Asp
        610             615             620
Thr Asp Ser Ile Tyr Cys Asn Arg Glu Val Asn Ser Leu Ile Glu Asp
625             630             635                 640
Met Asn Ala Ile Gly Glu Thr Ile Asp Lys Thr Ile Leu Gly Lys Trp
            645             650                 655
Asp Val Glu His Val Phe Asp Lys Phe Lys Val Leu Gly Gln Lys Lys
            660             665                 670
Tyr Met Tyr His Asp Cys Lys Glu Asp Lys Thr Asp Leu Lys Cys Cys
            675             680                 685
Gly Leu Pro Ser Asp Ala Arg Lys Ile Ile Gly Gln Gly Phe Asp
            690             695             700
Glu Phe Tyr Leu Gly Lys Asn Val Glu Gly Lys Lys Gln Arg Lys Lys
705             710             715                 720
Val Ile Gly Gly Cys Leu Leu Leu Asp Thr Leu Phe Thr Ile Lys Lys
                725             730                 735
Ile Met Phe

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Leu Ser Ala Glu Asn Leu Tyr Phe Gln Gly His His His His
1               5                   10                  15

His
```